United States Patent
Shinomiya et al.

(10) Patent No.: US 9,420,946 B2
(45) Date of Patent: Aug. 23, 2016

(54) INFORMATION PROVISION DEVICE, INFORMATION PROVISION SYSTEM, SERVER, INFORMATION PROVISION METHOD AND PROGRAM

(71) Applicant: NIKON CORPORATION, Tokyo (JP)

(72) Inventors: Takashi Shinomiya, Tokyo (JP); Nobuyuki Miyake, Hiratsuka (JP)

(73) Assignee: NIKON CORPORATION, Tokyo (JP)

( * ) Notice: Subject to any disclaimer, the term of this patent is extended or adjusted under 35 U.S.C. 154(b) by 0 days.

(21) Appl. No.: 14/389,634

(22) PCT Filed: Feb. 27, 2013

(86) PCT No.: PCT/JP2013/055146
§ 371 (c)(1),
(2) Date: Sep. 30, 2014

(87) PCT Pub. No.: WO2013/146040
PCT Pub. Date: Oct. 3, 2013

(65) Prior Publication Data
US 2015/0070349 A1    Mar. 12, 2015

(30) Foreign Application Priority Data

Mar. 30, 2012    (JP) ................................. 2012-080338

(51) Int. Cl.
*A61B 3/00* (2006.01)
*A61B 3/08* (2006.01)
(Continued)

(52) U.S. Cl.
CPC ............... *A61B 3/08* (2013.01); *A61B 3/0025* (2013.01); *A61B 3/0041* (2013.01); *A61B 3/028* (2013.01); *A61B 3/09* (2013.01)

(58) Field of Classification Search
None
See application file for complete search history.

(56) References Cited

U.S. PATENT DOCUMENTS

2005/0190180 A1*  9/2005  Jin .................... H04N 13/0018
                                                345/419
2010/0033678 A1*  2/2010  Foster ..................... A61B 3/18
                                                351/223

(Continued)

FOREIGN PATENT DOCUMENTS

JP      S62-27916 A     2/1987
JP      H10-52402 A     2/1998

(Continued)

OTHER PUBLICATIONS

"Guidelines for Workplace Health Management in VDT Work". Apr. 5, 2002.

(Continued)

*Primary Examiner* — Kee M Tung
*Assistant Examiner* — Ryan M Gray
(74) *Attorney, Agent, or Firm* — Oliff PLC

(57) ABSTRACT

A user can know the level of his/her own binocular vision. When an input instruction is input by the user via an input part, an information management part outputs a test request to a testing device, and a determination processing part obtains test results output from the testing device. The determination processing part determines a total level based on the test results and on information stored in a storage part. The determination processing part outputs the obtained total level to an output processing part. The output processing part generates a display screen in which the obtained total level and indices associated with the total level are written. The output processing part outputs the generated display screen to a display part. This causes the display part to display the display screen, and the user can know the concrete level of his/her own binocular vision.

12 Claims, 21 Drawing Sheets

(51) Int. Cl.
*A61B 3/028* (2006.01)
*A61B 3/09* (2006.01)

(56) References Cited

U.S. PATENT DOCUMENTS

| | | |
|---|---|---|
| 2010/0177278 A1 | 7/2010 | Reichow et al. |
| 2010/0191582 A1* | 7/2010 | Dicker ............... G06Q 30/02 705/14.51 |
| 2011/0310093 A1* | 12/2011 | Kwak ............... H04N 13/0033 345/419 |
| 2012/0068998 A1* | 3/2012 | Hong ............... A61B 3/032 345/419 |
| 2012/0105609 A1* | 5/2012 | Qi ............... A61B 3/08 348/54 |

FOREIGN PATENT DOCUMENTS

| | | |
|---|---|---|
| JP | H1156780 A | 3/1999 |
| JP | 2004329795 A | 11/2004 |
| JP | 2008086657 A | 4/2008 |
| JP | 2010523290 A | 7/2010 |
| JP | 2010193411 A | 9/2010 |
| JP | 2013030853 A | 2/2013 |

OTHER PUBLICATIONS

Mar. 26, 2013 Search Report issued in International Application No. PCT/JP2013/055146.

* cited by examiner

FIG. 2

| TEST ITEM / ID | BASIC STEREOSCOPIC VISION | | TOLERANCE AND PHYSIOLOGICAL BASIC ELEMENTS | | | | | |
|---|---|---|---|---|---|---|---|---|
| | STEREO TEST (SOA) | ACCOMMO-DATION TIME MEASURING TEST (sec.) | FLICKER TEST (Hz) | DURATION MEASURING TEST (sec.) | BREAK STRENGTH MEASURING TEST (Δ) | LEFT/RIGHT EYE ROTATION ANGLE MEASURING TEST (°) | VISUAL DEPTH ACUITY MEASURING TEST (cm) | ... |
| 00001 | 800 | 3.0 | 42 | 720 | LEFT-RIGHT: 16.00 UP-DOWN: 4.75 | 1.0 | 1.5 | |

FIG. 3

DETERMINATION TABLE 121

| TEST ITEM / BASIC LEVEL | BASIC STEREOSCOPIC VISION | | TOLERANCE AND PHYSIOLOGICAL BASIC ELEMENTS | | | | |
|---|---|---|---|---|---|---|---|
| | STEREO TEST (SOA) | ACCOMMO-DATION TIME MEASURING TEST (sec.) | FLICKER TEST (Hz) | DURATION MEASURING TEST (sec.) | BREAK STRENGTH MEASURING TEST (Δ) | LEFT/RIGHT EYE ROTATION ANGLE MEASURING TEST (°) | VISUAL DEPTH ACUITY MEASURING TEST (cm) | ... |
| LEVEL v | <750 | <5.0 | 40≦ | 600≦ | LEFT-RIGHT:15≦ UP-DOWN:4≦ | <0.5 | <1.0 |
| LEVEL iv | 750≦x<1500 | 5≦x<10 | 37≦x<40 | 300≦x<600 | LEFT-RIGHT:11≦x<15 UP-DOWN:3≦x<4 | 0.5≦x<0.7 | 1.0≦x<1.5 |
| LEVEL iii | 1500≦x<3000 | 10≦x<15 | 34≦x<37 | 60≦x<300 | LEFT-RIGHT:7≦x<11 UP-DOWN:2≦x<3 | 0.7≦x<1.0 | 1.5≦x<2.0 |
| LEVEL ii | 3000≦ | 15≦x<60 | 30≦x<34 | 10≦x<60 | LEFT-RIGHT:4≦x<7 UP-DOWN:1≦x<2 | 1.0≦x<2.0 | 2.0≦x<4.0 |
| LEVEL i | UNIDENTIFI-ABLE | 60≦ | <30 | <10 | LEFT-RIGHT:<4 UP-DOWN:<1 | 3.0≦ | 4.0≦ |

FIG. 4

SCORE TABLE 122

| BASIC LEVEL | LEVEL i | LEVEL ii | LEVEL iii | LEVEL iv | LEVEL v |
|---|---|---|---|---|---|
| TEMPORARY SCORE POINT | 0 | 25 | 50 | 75 | 100 |

WEIGHTING COEFFICIENT TABLE 123

| TEST ITEM | BASIC STEREOSCOPIC VISION | | TOLERANCE AND PHYSIOLOGICAL BASIC ELEMENTS | | | | ... |
| --- | --- | --- | --- | --- | --- | --- | --- |
| | STEREO TEST (SOA) | ACCOMMO-DATION TIME MEASURING TEST (sec.) | FLICKER TEST (Hz) | DURATION MEASURING TEST (sec.) | BREAK STRENGTH MEASURING TEST (Δ) | LEFT/RIGHT EYE ROTATION ANGLE MEASURING TEST (°) | VISUAL DEPTH ACUITY MEASURING TEST (cm) |
| WEIGHTING COEFFICIENT | 0.5 | 0.2 | 0.06 | 0.08 | 0.08 | 0.05 | 0.03 |

TOTAL DETERMINATION TABLE 124

| TOTAL LEVEL | TOTAL SCORE REFERENCE RANGE | INDEX | |
| --- | --- | --- | --- |
| | | 3D IMAGE INTENSITY | 3D IMAGE VIEWING TIME/DAY |
| LEVEL I | 80≦ | HIGH | LESS THAN 4 HOURS |
| LEVEL II | 60≦x<80 | INTERMEDIATE | LESS THAN 4 HOURS |
| LEVEL III | 40≦x<60 | INTERMEDIATE | LESS THAN 3 HOURS |
| LEVEL IV | 20≦x<40 | LOW | LESS THAN 2 HOURS |
| LEVEL V | <20 | INCAPABLE OF BINOCULAR VISION | INCAPABLE OF BINOCULAR VISION |

FIG. 12

PRODUCT LIST 125

| PRODUCT NAME | TOTAL LEVEL | TYPE | PRODUCT GUIDE INFORMATION |
|---|---|---|---|
| VVV | LEVEL V | DVD | FEATURES REALISTIC AND POWERFUL 3D IMAGES |
| WWW | LEVEL II | DVD | 3D MOVIE FOR KIDS |
| XXX | LEVEL IV | CAMERA | 3D CAMERA FOR PHOTOGRAPHING REALISTIC AND POWERFUL 3D IMAGES |
| YYY | LEVEL III | CAMERA | EASY-TO-USE 3D CAMERA |
| ... | ... | ... | ... |

TEST RESULT LIST 231

| USER INFORMATION | | TEST RESULT | | | | | | |
|---|---|---|---|---|---|---|---|---|
| | | BASIC STEREOSCOPIC VISION | | TOLERANCE AND PHYSIOLOGICAL BASIC ELEMENTS | | | | |
| USER NAME | USER ID | STEREO TEST (SOA) | ACCOMMO-DATION TIME MEASURING TEST (sec.) | FLICKER TEST (Hz) | DURATION MEASURING TEST (sec.) | BREAK STRENGTH MEASURING TEST (Δ) | LEFT/RIGHT EYE ROTATION ANGLE MEASURING TEST (°) | VISUAL DEPTH ACUITY MEASURING TEST (cm) |
| XXX | 1 | 800 | 3.0 | 42 | 720 | LEFT-RIGHT: 16.00 UP-DOWN: 4.75 | 1.0 | 1.5 |
| ... | ... | ... | ... | ... | ... | ... | ... | ... |

2311     2312

INFORMATION PROVISION DEVICE, INFORMATION PROVISION SYSTEM, SERVER, INFORMATION PROVISION METHOD AND PROGRAM

TECHNICAL FIELD

The present invention relates to an information presenting device, an information presenting system, a server, an information presenting method, and a program with which information depending on the level of binocular vision is presented. The present invention claims priority to Japanese Patent Application No. 2012-80338 filed on Mar. 30, 2012, the content of which is incorporated herein in its entirety by reference in designated states where incorporation by reference of literature is allowed.

BACKGROUND ART

In recent years, technologies of providing three-dimensional images (still images and moving images) which have a stereoscopic effect and a sense of depth to the viewer's eye are becoming popular. However, not everyone possesses the ability to perceive three-dimensional pictures having such properties (binocular vision). Binocular vision in general is broken into simultaneous perception, fusion, and stereoscopic vision. Simultaneous perception is a function of merging and simultaneously viewing different images on the left retina and the right retina. Fusion is a function of fusing substantially the same retinal images at retinal corresponding points on the left eye and the right eye, and perceiving the images as a single object. Stereoscopic vision is a function of perceiving a stereoscopic effect from a disparity between the images due to binocular parallax after fusion is established. A viewer who has a problem with these functions cannot enjoy three-dimensional images. In addition, because visuoperceptual phenomena of this type are personal and subjective, sharing/comparing with others is difficult, which hinders a person with defective binocular vision from recognizing the defect.

In Cited Document 1, there is proposed a stereoscopic vision testing device for determining whether or not a subject's stereoscopic vision is sound based on whether or not the subject is capable of recognizing a three-dimensional-index image. Stereoscopic vision is an ability to perceive an object stereoscopically through the fusion of binocular images, specifically, an ability to sense a slight difference in depth between two points through the fusion of binocular images. Stereoscopic vision is hereinafter referred to as binocular vision.

CITATION LIST

Patent Literature

[PTL 1] Japanese Patent Laid-open Publication No. H11-056780

SUMMARY OF INVENTION

Technical Problem

The invention described in Cited Document 1, however, is only capable of determining whether a subject's binocular vision is sound or not, and does not tell how good a subject's binocular vision is.

Differences in the level of binocular vision are considered as a factor for the variation in the degree of strain felt by workers who use their stereoscopic vision in visual display terminal (VDT) work, and the variation in the length of time that the workers can continue working at VDTs. VDT workers therefore need to know the levels of their own binocular vision.

In video games, movies, and other digital contents that are currently generated, the range of parallax in the depth direction (toward the front of the screen and toward the back of the screen) has a small value (for example, the maximum value of the parallax is 2 degrees) so that viewers with weak binocular vision can enjoy as well. The range of parallax in the depth direction (toward the front of the screen and toward the back of the screen) of an image is hereinafter referred to as three-dimensional intensity. High three-dimensional intensity means that the range of parallax in the depth direction (toward the front of the screen and toward the back of the screen) is wide, i.e., that the maximum value of the parallax in the depth direction (toward the front of the screen and toward the back of the screen) is large. Low three-dimensional intensity means that the range of parallax in the depth direction (toward the front of the screen and toward the back of the screen) is narrow, i.e., that the maximum value of the parallax in the depth direction (toward the front of the screen and toward the back of the screen) is small.

However, such digital contents are hardly enjoyable to viewers with great binocular vision. It is therefore desirable to prepare different versions of the same digital contents which differ in three-dimensional intensity so that a viewer can know the level of his/her own binocular vision and can select by himself/herself a version of the digital contents that is suitable for his/her own binocular vision.

The present invention has been made in view of those circumstances, and an object of the present invention is to provide an information presenting device, an information presenting system, a server, and an information presenting method, and a program with which figuring out the level of binocular vision is easy.

Solution to Problem

The present invention has been made in order to achieve the above-mentioned object, and an information presenting device according to one embodiment of the present invention includes, for example: an obtaining part adapted to obtain results of tests related to a user's binocular vision; a classifying part adapted to classify, based on the obtained test results, the user's binocular vision into one of a plurality of classes; and an output part adapted to output information suited to the user's binocular vision, based on the class into which the user's binocular vision is classified, to display part.

Further, in the information presenting device according to one embodiment of the present invention, it is desired that the test results obtained by the obtaining part include results of at least two test items selected from a stereo test, an accommodation time measuring test, a flicker test, a duration measuring test, a break strength measuring test, a left/right eye rotation angle measuring test, and a visual depth acuity measuring test, and that the classifying part calculates a temporary score point for each of the at least two test items, calculate a score based on the calculated temporary score points, and classify the user's binocular vision into one of the plurality of classes based on the calculated score.

Further, in the information presenting device according to one embodiment of the present invention, it is desired that the classifying part calculates the score by multiplying the temporary score points by weighting coefficients that are associated with the test items, and adding up the weighted score points.

Further, in the information presenting device according to one embodiment of the present invention, it is desired that the output part outputs, as the information suited to the user's binocular vision, information that indicates the class into which the user's binocular vision is classified.

Further, it is desired that the information presenting device according to one embodiment of the present invention further include: a storage part adapted to store information related to a product in association with an appropriate one of the plurality of classes; and a product determining part adapted to determine a product suitable for the user based on the class into which the user's binocular vision is classified and the information stored in the storage part, and that the output part outputs information related to the determined product as the information suited to the user's binocular vision.

Further, in the information presenting device according to one embodiment of the present invention, it is desired that the information related to a product be at least one of a product name, a product type, and information introducing the product.

Further, it is desired that the information presenting device according to one embodiment of the present invention further include: a Web server for providing a Web page; input part adapted to input a request to view detailed information of the determined product; and Web page obtaining part adapted to obtain, when the viewing request is input by the input part, a Web page that contains a description about the determined product from the Web server, and that the output part outputs the obtained Web page to the display part.

It is desired that the information presenting device according to one embodiment of the present invention further include: a two-dimensional image obtaining part adapted to obtain two-dimensional images; and a three-dimensional image generating part adapted to generate, based on the class into which the user's binocular vision is classified, from the obtained two-dimensional images, a three-dimensional image suitable for the class of binocular vision into which the user's binocular vision is classified, and that the output part outputs the generated three-dimensional image as the information suited to the user's binocular vision.

In the information presenting device according to one embodiment of the present invention, it is desired that the three-dimensional image generating part generates a three-dimensional image so that a parallactic angle associated with the class into which the user's binocular vision is classified by the classifying part is reached.

Further, an information presenting system according to one embodiment of the present invention includes, for example: a terminal device; and a server connected to the terminal device, the server comprising: an obtaining part adapted to obtain results of tests related to a user's binocular vision; a classifying part adapted to classify, based on the obtained test results, the user's binocular vision into one of a plurality of classes; and an output part adapted to output information suited to the user's binocular vision, based on the class into which the user's binocular vision is classified, to the terminal device.

It is desired that the information presenting system according to one embodiment of the present invention further include a Web server for providing a Web page, that the server further include: a storage part adapted to store information related to a product in association with an appropriate one of the plurality of classes; a product determining part adapted to determine a product suitable for the user based on the class into which the user's binocular vision is classified and the information stored in the storage part; and a Web page obtaining part adapted to obtain a Web page that contains a description about the determined product from the Web server, and that the output part adapted to output the obtained Web page to the terminal device as the information suited to the user's binocular vision.

Note that, the present invention can also provide a server that is a constituent of the information presenting system.

An information presenting method according to one embodiment of the present invention includes, for example, the steps of: obtaining results of tests related to a user's binocular vision; classifying, based on the obtained test results, the user's binocular vision into one of a plurality of classes; and outputting information suited to the user's binocular vision, based on the class into which the user's binocular vision is classified.

A program according to one embodiment of the present invention causes, for example, a computer to function as an information presenting device, the program causing the computer to execute the steps of: obtaining results of tests related to a user's binocular vision; classifying, based on the obtained test results, the user's binocular vision into one of a plurality of classes; and outputting information suited to the user's binocular vision, based on the class into which the user's binocular vision is classified.

Advantageous Effects of Invention

The present invention has been made in view of those circumstances, and the level of binocular vision can be easily figured out.

BRIEF DESCRIPTION OF DRAWINGS

FIG. 2 is a schematic explanatory diagram of test results obtained.

FIG. 3 is a schematic explanatory diagram of a determination table 121.

FIG. 4 is a schematic explanatory diagram of a score table 122.

FIG. 5 is a schematic explanatory diagram of a weighting coefficient table 123.

FIG. 6 is a schematic explanatory diagram of a total determination table 124.

FIG. 12 is a schematic explanatory diagram of a product list 125.

FIG. 13 is a flow chart illustrating processing that is executed by a control part 11a.

FIG. 19 is a schematic explanatory diagram of a test result list 231.

DESCRIPTION OF EMBODIMENTS

Now, embodiments of the present invention are described with reference to the drawings.

First Embodiment

Figure 1:
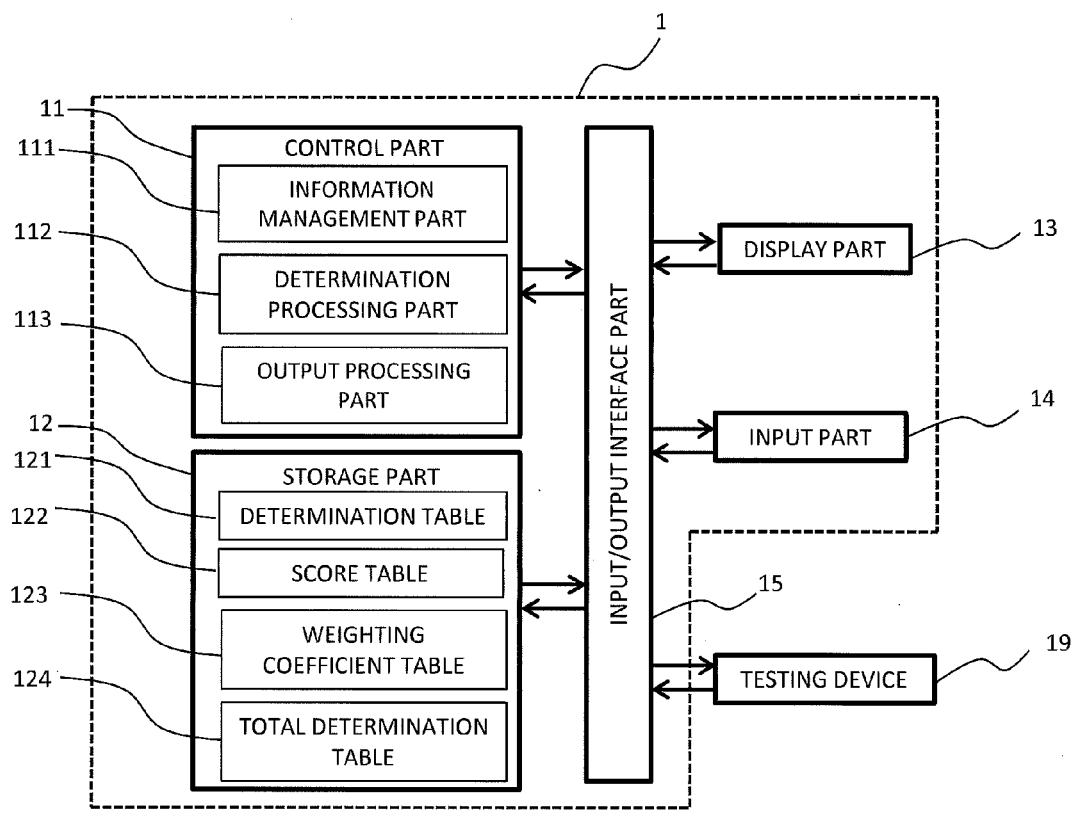
FIG. 1 is a schematic configuration diagram illustrating the configuration of an information presenting device 1 according to a first embodiment of the present invention.

FIG. 1 is a schematic configuration diagram illustrating the configuration of an information presenting device 1. The information presenting device 1 is a device for obtaining the results of tests related to binocular vision, evaluating systematically and comprehensively a user's binocular vision, in particular, fusion and stereoscopic vision, based on the obtained test result data, and outputting the result of the evaluation.

The information presenting device 1 is a terminal set up at a storefront, in a workplace, in a user's home, or the like, or a portable terminal carried by a sales clerk, a user, or others, and includes a control part 11, a storage part 12, a display part 13, an input part 14, and an input/output interface part (hereinafter referred to as I/F part) 15. The information presenting device 1 is connected to one or more testing devices 19 directly or via a network (not shown). Not all components of the information presenting device 1 need to be in one place. For instance, the display part 13 and the input part 14 may be set up at a storefront to be connected by a wired or wireless network to the rest of the components which are set up at the back of the store or in an office.

The display part 13 is a liquid crystal display capable of displaying in colors, and displays based on information that is input from the control part 11. Display devices of other types such as an organic EL display may be used instead of a liquid crystal display.

The input part 14 includes a power button, an enter key, and others which are not shown, receives an operation instruction from a user, and sends operation information to the control part 11. A touch panel arranged at the front of the display part 13 may be used the input part 14. The input part 14 converts information such as the press of a particular button into various commands and outputs the commands to the control part 11 and other components.

The I/F part 15 connects one hardware component and another of the information presenting device 1, connects one function part and another of the information presenting device 1, and connects the information presenting device 1 and an external device in a manner that allows for signal transmission and reception. The I/F part 15 also provides an interface between a network (not shown) and the function parts.

The control part 11 includes an information management part 111 for handling overall information management, a determination processing part 112 for executing a determination program to determine stereoscopic vision from test results, and an output processing part 113 for outputting a result to the display part 13 based on the result of the determination. Here, the user himself/herself operates the information presenting device 1, but the information presenting device 1 may be operated by a person who is not a user.

The information management part 111 outputs a test request to each testing device 19 when a program is started. The testing device 19 receives the test request and conducts various tests such as ones described below. The testing device 19 may conduct other tests than the following as long as the tests relate to binocular vision. For instance, items "left/right eye rotation angle measuring test" and "visual depth acuity measuring test" may be dropped while tests for esophoria, exophoria, hyperphoria, hypophoria, and the like are added.

<Stereo Test>

A stereo test is a test for measuring whether or not a person has binocular vision, typically, the Titmus stereo test. Here, a target image (an image used in a general Titmus stereo test) is prepared by mixing a right-eye image and a left-eye image which have an intersecting or parallel parallax to be separated into a left image and a right image which are displayed on special polarized eyeglasses or a special monitor, and a user selects via the input part whether the image looks stereoscopic or not (whether the user's brain can perceive stereoscopic effect or not). The user's spectroscopic vision is obtained as a numerical value by using different parallactic angles (for example, 40" to 3,600") as a plurality of targets for target images. The user's binocular vision is classified at a higher level when the parallactic angle of a target image that the user can see stereoscopically is smaller.

<Accommodation Time Measuring Test>

An accommodation time measuring test is for measuring how long it takes for the user to see an image stereoscopically. A target image having a parallax is separated into images to be displayed on the special polarized eyeglasses or special monitor, the user inputs via the input part a time at which the image looks stereoscopically, and the length of time from the displaying of the image to the input (the time till the brain perceives stereoscopic effect) is measured. While any parallactic angle can be used (for example, 1,800" or so), it is desirable to use the same parallactic angle for all users. The user's binocular vision is classified at a higher level when the user requires a shorter accommodation time.

<Flicker Test>

A flicker test is one of strain measuring tests, and involves displaying a blinking target on a monitor, measuring a frequency at which the user sees the target as a constant light, and obtaining as a flicker value the frequency at which the target looks like a constant light (a threshold (flicker value) beyond which the intermittent light is no longer discernible and looks like a constant light). This can be regarded as a reference for resistance to eye strain, and the user's binocular vision is classified at a higher level when the flicker value is larger.

<Duration Measuring Test>

A duration measuring test is for measuring how long till fusion breaks. Here, a target image that does not have a parallax is displayed on special prism eyeglasses, a time at which multiple vision (fusion break) is perceived is received via the input part, and the length of time from the start of display till the perceiving of multiple vision is measured. The user's binocular vision is classified at a higher level when the duration is longer.

<Break Strength Measuring Test>

A break strength measuring test is for measuring a prism strength at which fusion breaks. A target image that does not have a parallax is displayed by the display part, the prism strength of special prism eyeglasses is changed continuously, a time at which multiple vision is perceived is received via the input part, and the prism strength (diopter value) at this point is measured. The user's binocular vision is classified at a higher level when the prism strength is higher.

<Left/Right Eye Rotation Angle Measuring Test>

A left/right eye rotation angle measuring test is for measuring whether there is cyclophoria, which is deviation in the clockwise or counterclockwise rotation of an eyeball, and for measuring the amount of the rotation. A "clock" target image is prepared by combining two monocular target images (a cross target and a circular target), and is separated into an image for the left eye and an image for the right eye which are displayed on special eyeglasses one at a time. A scale mark on the circular target that is pointed by the cross target is received via the input part, and the amounts of deviation (rotation amounts) of the left eye and the right eye are measured. The user's binocular vision is classified at a higher level when the rotation amount is smaller.

<Visual Depth Acuity Measuring Test>

A visual depth acuity measuring test is a test for stereoscopic vision, typically, the "three-culm method". In the three-culm method, a movable culm (rod) sandwiched between two stationary culms (rods) travels to and fro in the depth direction, and an error between a point at which the three are perceived to be aligned side by side and a point at which the three are actually aligned side by side is measured. The information presenting device 1 obtains the result of a test conducted with a depth perception testing machine that uses the three-culm method that has hitherto been practiced. The user's binocular vision is classified at a higher level when the error is smaller.

The testing device 19 outputs test results as those shown in FIG. 2 to the information presenting device 1. As shown in FIG. 2, the results of the respective tests are shown quantitatively in numerical values. In the case where the user already knows test results, the test results may be input by the user via the input part 14.

The determination processing part 112 obtains the test results (see FIG. 2) output from the testing device 19, or input via the input part 14, and determines to which class (total level) the user's binocular vision belongs. Details of the processing of the determination processing part 112 are described later.

The output processing part 113 generates an output screen, which is to be displayed by the display part 13, based on the result of the determination made by the determination processing part 112, and outputs the generated output screen to the display part 13. Details of the processing of the output processing part 113 are described later.

The storage part 12 stores in advance a determination table 121, which serves as a reference for evaluating a basic level in each test item, a score table 122 and a weighting coefficient table 123, which are used for converting the basic level in each test item into a score point, and a total determination table 124, which is used for determining the total stereoscopic vision level from a score point.

FIG. 3 is a schematic explanatory diagram of the determination table 121. The determination table 121 is referred to in the determination of a basic level based on a test item, and includes a level storing area 1211 and a reference range storing area 1212. The level storing area 1211 stores basic levels as arbitrary classes. The reference range storing area 1212 stores a reference range for each test item and for each basic level of a test result in the test item.

Basic levels are set by dividing test result values into reference ranges. In this embodiment, there are five basic levels, Level i to Level v, of which Level v has the best test result and Level i has the poorest test result.

Reference ranges at the respective basic levels have been determined by dividing, into classes, based on relative frequency, results of a test by distribution in which the general public is assumed as the parental population, in other words, a test that has been conducted on a population consisting of the general public. Specifically, Level i is a group of people who make up approximately 5% of the total and who are estimated to be incapable of stereoscopic vision (but are capable of monocular vision). Level ii is a group of people who make up approximately 15% of the total and who manage to sustain stereoscopic vision for a very short length of time (less than 10 minutes) with effort, or are estimated to be able to enhance their stereoscopic vision with training. Level iii is a group of people who make up approximately 30% of the total, and who are estimated to be capable of sustaining stereoscopic vision for a short length of time (around 15 to 30 minutes) without difficulty. Level iv is a group of people who make up approximately 40% of the total, and who are estimated to be capable of sustaining stereoscopic vision for an intermediate length of time (around 30 to 60 minutes) without difficulty. Level v is a group of people who make up approximately 10% of the total, and who are estimated to be capable of sustaining stereoscopic vision for long (an hour or longer) without difficulty. The stereoscopic vision here is with respect to a still image, but the basic levels can of course be set with respect to a moving image as well.

The reference range storing area 1212 is provided with a parallactic angle storing area 1212a for storing reference ranges for the stereo test, an accommodation time storing area 1212b for storing reference ranges for the accommodation time measuring test, a flicker value storing area 1212c for storing reference ranges for the flicker test, a duration storing area 1212d for storing reference ranges for the duration measuring test, a break strength storing area 1212e for storing reference ranges for the break strength measuring test, a rotation angle storing area 1212f for storing reference ranges for the left/right eye rotation angle measuring test, and an average error storing area 1212g for storing reference ranges for the visual depth acuity measuring test.

The basic levels are, by definition, determined from reference ranges of test results, and do not need to have the count of classes shown in FIG. 3. The same applies to reference ranges and to indices described later. Reference ranges and the indices can be set arbitrarily based on medical findings, experiences, the statistics of accumulated data, and the like.

FIG. 4 is a schematic explanatory diagram of the score table 122. The score table 122 includes a basic level storing area 1221 for storing the respective basic levels, and a score storing area 1222 for storing for each basic level a temporary score point.

FIG. 5 is a schematic explanatory diagram of the weighting coefficient table 123. The weighting coefficient table 123 includes a test item storing area 1231 for storing the respective test items, and a weighting coefficient storing area 1232 for storing a weighting coefficient for each test item. These are used in the calculation of a total score.

The total score is a solution obtained by obtaining, from the score table 122, for each test item, a temporary score point of the basic level in the test item, multiplying the temporary score point by a weighting coefficient of the test item, and adding up the weighted score points of the respective test items. Specifically, the score table 122 shows that the temporary score point is 0 points for Level i and 100 points for Level v. In this embodiment, where seven test items are laid down, the sum of temporary score points in the respective test items is 700 points (when the basic level is Level v in every test item). The temporary score points in the respective test items are each multiplied by a relevant weighting coefficient stored in the weighting coefficient table 123, and the sum of the weighted score points constitutes the total score.

Multiplying score points of the respective basic levels by the weighting coefficients stored in the weighting coefficient table in this manner ultimately gives different levels of importance to the respective test items. For instance, weighting in the weighting coefficient table 123 according to this embodiment puts emphasis on stereoscopic vision. Specifically, results of tests belonging to a first group which are test items related mainly to stereoscopic vision (the stereo test and the accommodation time measuring test) make up 70% of the full points of the total score, whereas results of the remaining tests belonging to a second group which are test items related to tolerance and physiological elements (the flicker test, the duration measuring test, the break strength measuring test, the left/right eye rotation angle measuring test, and the visual depth acuity measuring test) make up merely 30% of the full points of the total score (the total score is adjusted so that the full score is 100 points). Evaluation that puts emphasis on stereoscopic vision is thus made.

The emphasis of evaluation can be put on various other visions. A plurality of weighting coefficient tables may therefore be prepared to be switched from one to another depending on the purpose of the test. The classification of test items and weighting coefficients of the test items can also be set arbitrarily based on medical findings, experiences, the statistics of accumulated data, and the like. While a weighting coefficient is set for each test item here, a weighting coefficient may be set for each test item group described above to be used in the calculation of the total score.

FIG. 6 is a schematic explanatory diagram of the total determination table 124. The total determination table 124 includes a total level storing area 1241 for storing total levels indicating total stereoscopic vision, a total score reference range storing area 1242 for storing for each total level a reference range of the total score, and an index storing area 1243 for storing for each total level information indicating an index.

Total levels are evaluation levels of binocular vision determined from the total score. The total levels in this embodiment are five levels, Level I to Level V, of which Level I indicates the best binocular vision and Level V indicates the poorest binocular vision. In FIG. 6, for example, the total level is classified as I when the total score is 80 points or higher, and is classified as V when the total score is lower than 20 points.

An index is information that indicates a subject's stereoscopic vision concretely, and various types of information can be used as indices. The indices employed in FIG. 6 are the intensity of a three-dimensional image that can be viewed by the subject, and the length of three-dimensional image viewing time per day. For instance, in the case where the total level is I, a 3D image having "high" intensity can be viewed and it is recommended to keep the total length of 3D image viewing time for a day under four hours. In the opposite case where the total level is V, the subject is incapable of binocular vision and cannot view a 3D image.

This embodiment is not limited to these indices, and indices that follow existing guidelines having a scientific and physiological basis, such as "Guidelines for Workplace Health Management in VDT Work" (2002, Japanese Ministry of Health, Labour and Welfare) may be created.

Figure 7:
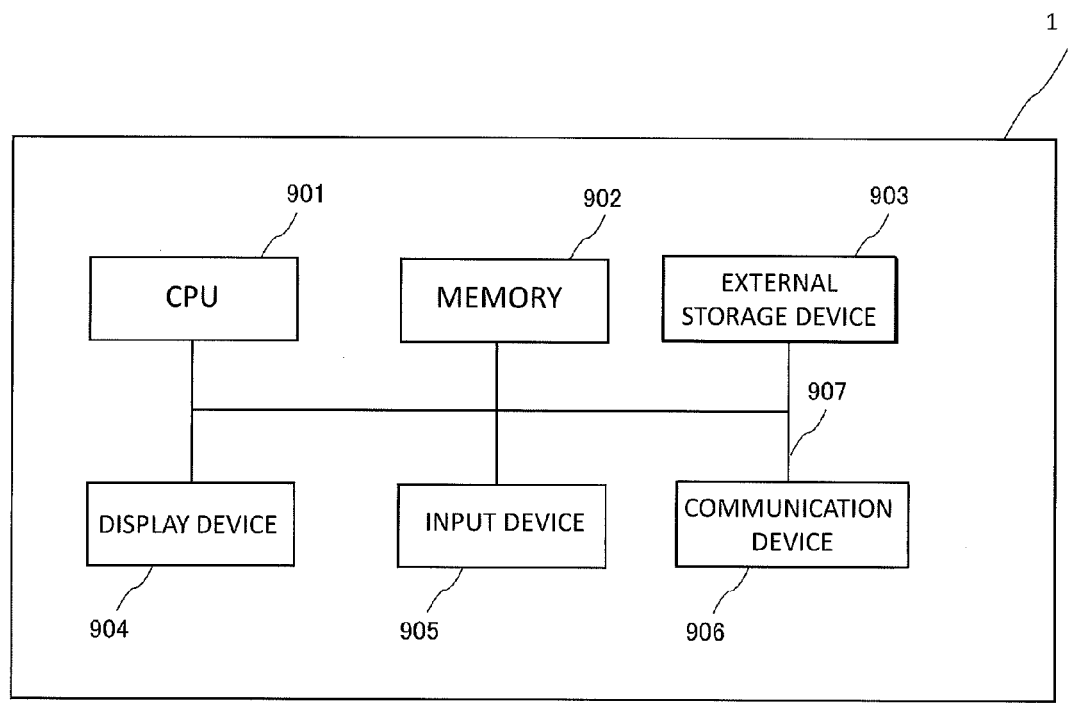
FIG. 7 is a block diagram illustrating the hardware configuration of the information presenting devise 1.

The hardware configuration of the information presenting device 1 is now described. FIG. 7 is a block diagram illustrating the electrical configuration of the information presenting device 1.

The information presenting device 1 includes a central processing unit (CPU) 901 for controlling the respective components in a centralized manner, a memory 902 for storing various types of data in a manner that allows for rewrite, an external storage device 903 for storing various programs, data generated by the programs, and others, a display device 904, which is constructed from a liquid crystal display device, an organic electroluminescence (EL) display, or the like, an input device 905, which is constructed from a keyboard, a mouse, a touch panel, or the like, a communication device 906, which is, for example, a network interface card (NIC) for connecting to a communication network, and a bus 907 for connecting these components.

The control part 11 can be implemented by loading a given program which is stored in the external storage device 903 onto the memory 902 and executing the program with the CPU 901. The storage part 12 can be implemented by the CPU 901 by using the memory 902 or the external storage device 903. The display part 13 can be implemented by the CPU 901 by using the display device 904. The input part 14 can be implemented by the CPU 901 by using the input device 905. The I/F part 15 can be implemented by the CPU 901 by using the communication device 906.

The components are classified by the specifics of their main processing in order to help understand the configuration of the information presenting device 1. The present invention is not limited by the way processing steps are classified or the names of the processing steps. Processing executed by the information presenting device 1 may be broken into more components depending on the specifics of the processing. Processing of the information presenting device 1 may also be classified so that more processing procedures are executed per component.

The function parts may be built from hardware (ASIC and the like). Processing of the respective function parts may be executed by a single piece of hardware, or a plurality of pieces of hardware.

Figure 8:
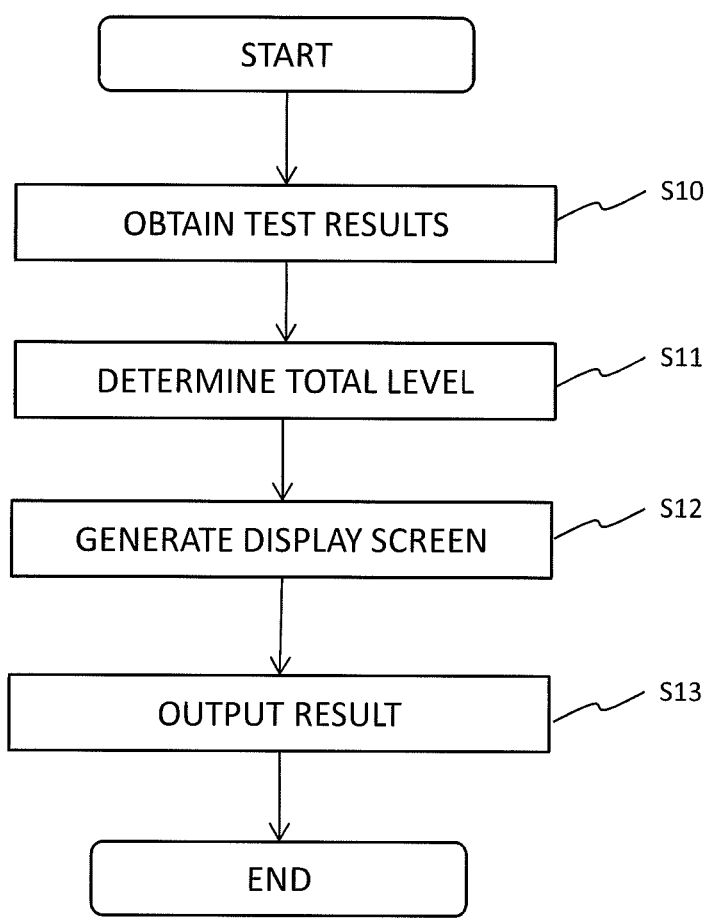
FIG. 8 is a flow chart illustrating processing that is executed by a control part 11.
Figure 9:
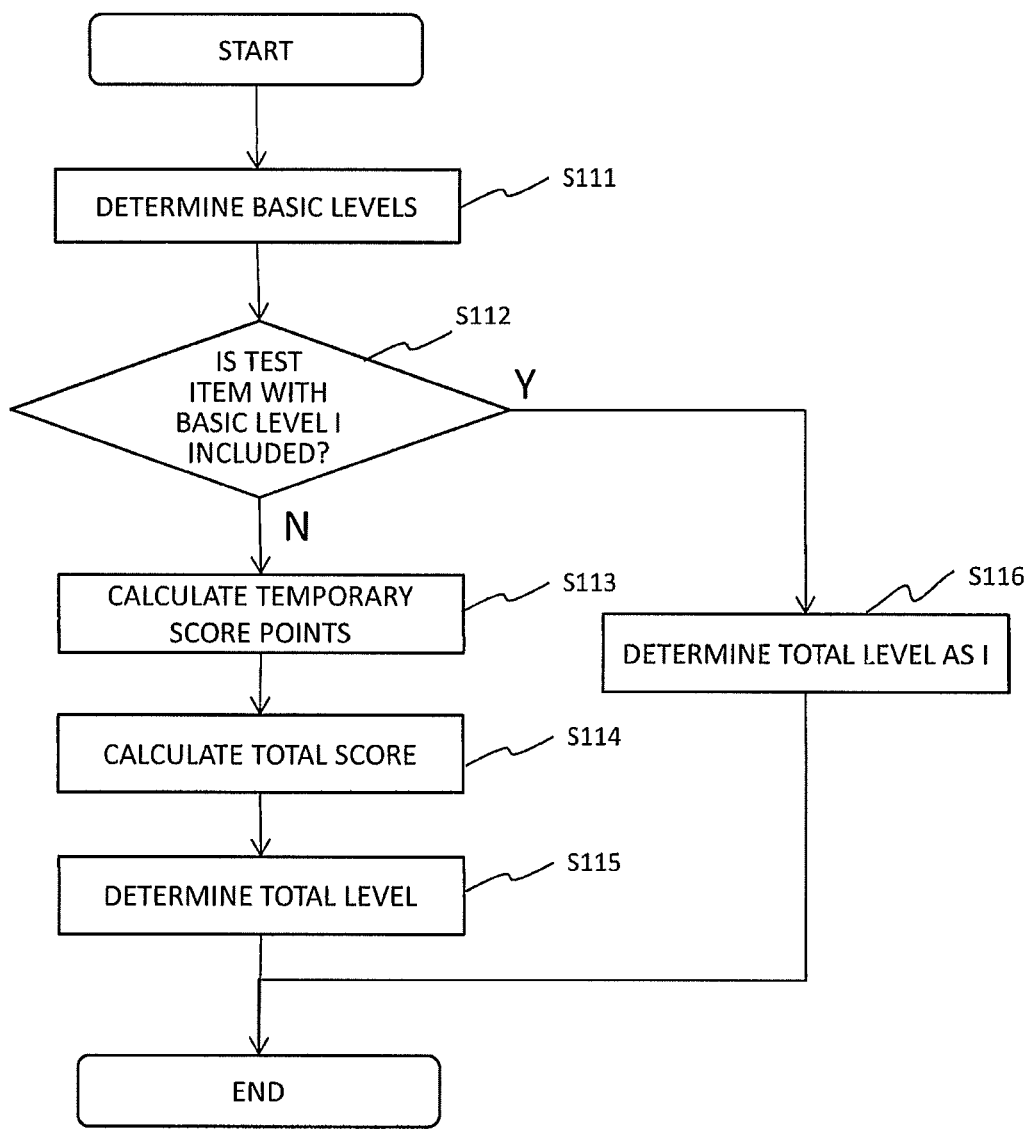
FIG. 9 is a flow chart illustrating the flow of determination processing which is executed by a determination processing part 112.

The operation of the thus configured information presenting device 1 is described with reference to flow charts of FIG. 8 and FIG. 9. FIG. 8 is a flow chart illustrating the flow of processing that is executed by the information presenting device 1 according to this embodiment.

When an input instruction is input by a user via the input part 14, the information management part 111 receives the instruction and outputs a test request to the testing device 19, and the determination processing part 112 obtains test results (see FIG. 2) output from the testing device 19 (Step S10).

The determination processing part 112 temporarily stores the obtained test results in the memory 902, and determines the total level based on the test results and on information stored in the storage part 12 (Step S11). FIG. 9 is a flowchart illustrating the processing flow of the total level determination processing (Step S11) which is executed by the determination part 112.

The determination processing part 112 refers to the determination table 121 to determine a basic level for each test result (S111). For example, in the case where the obtained test results are those of FIG. 2, the basic levels of the respective test results are as follows. The basic level of the stereo test where the score is "800 SOA" is Level iv. The basic level of the accommodation time measuring test where the score is "3 seconds" is Level v. The basic level of the flicker test where the score is "42 Hz" is Level v. The basic level of the duration measuring test where the score is "720 seconds" is Level v. The basic level of the break strength measuring test where the score is "16" for left-right and "4.75" for up-down is Level v. The basic level of the left/right eye rotation angle measuring test where the score is "1.0°" is Level ii. The basic level of the visual depth acuity measuring test where the score is "1.5 cm" is Level iii.

The determination processing part 112 determines whether or not the result of the determination in Step S111 includes a test item whose basic level is Level i (S112).

In the case where a test item whose basic level is Level is included (YES in S112), the total level is determined as Level I (S116), and the determination processing is ended.

In the case where a test item whose basic level is Level i is not included (NO in S112), the determination processing part 112 refers to the score table 122 to convert each basic level into a temporary score point (S113). For example, in the case where the obtained test results are those of FIG. 2, temporary score points based on the basic levels that have been obtained in Step S111 are as follows. The temporary score point of the stereo test where the basic level is Level iv is 75 points. The temporary score point of the accommodation time measuring test where the basic level is Level v is 100 points. The temporary score point of the flicker test where the basic level is Level v is 100 points. The temporary score point of the duration measuring test where the basic level is Level v is 100 points. The temporary score point of the break strength measuring test where the basic level is Level v is 100 points. The temporary score point of the left/right eye rotation angle measuring test where the basic level is Level ii is 25 points. The temporary score point of the visual depth acuity measuring test where the basic level is Level iii is 50 points.

The determination processing part 112 refers to the weighting coefficient table 123 to multiply the temporary score points calculated in Step S113 by their respective weighting coefficients, and adds up the weighted values to obtain a total score (S114). For example, in the case where the obtained test results are those of FIG. 2, the total score is calculated from the temporary score points obtained in Step S113 and the weighting coefficient table 123 of FIG. 5 as follows.

$$(75 \times 0.5)+(100 \times 0.2)+(100 \times 0.06)+(100 \times 0.08)+(100 \times 0.08)+(25 \times 0\ 0.05)+(50 \times 0.03)=82.5$$

The determination processing part 112 refers to the total determination table 124 to determine the total level (S115), and ends the determination processing. When the total score is 82.25 points in Step S114, the total level determined with reference to the total determination table 124 of FIG. 6 is Level V.

Referring back to FIG. 8, after the total level determination processing (Step S11) is finished in this manner, the determination processing part 112 outputs the obtained total level to the output processing part 113, which generates, based on the total level output from the determination processing part 112, a screen showing the output total level and indices that are associated with the total level (a display screen 130) (Step S12).

Figure 10:
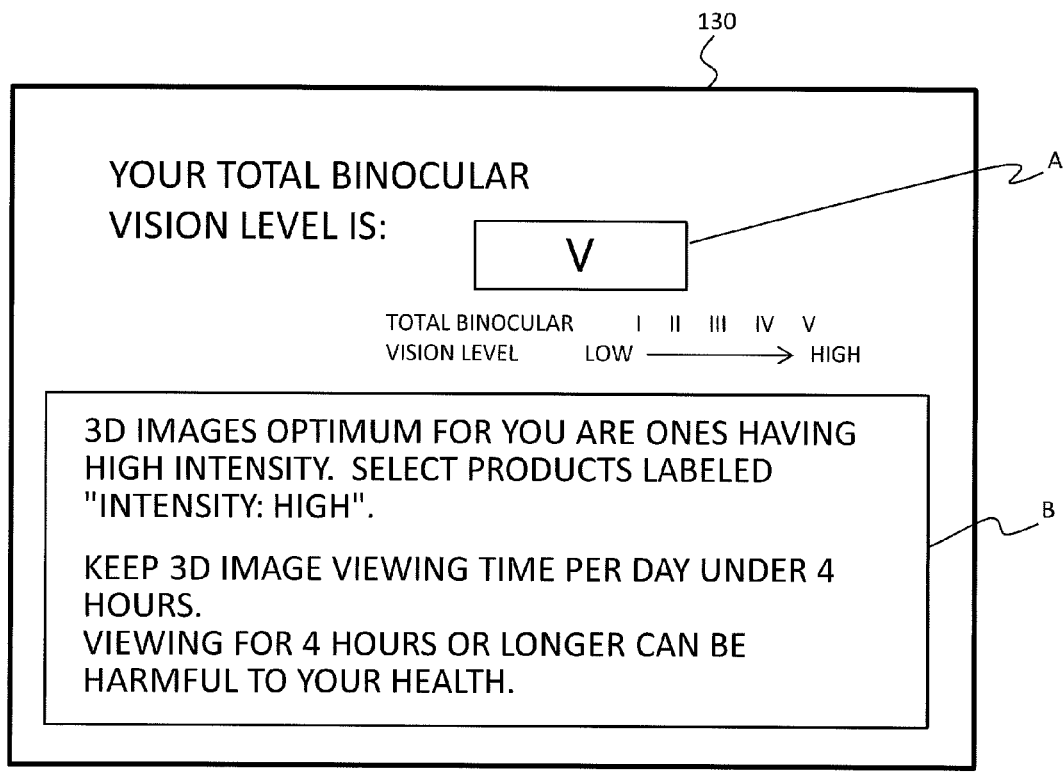
FIG. 10 is a schematic view of a display screen 130.

FIG. 10 is an example of the display screen 130. The display screen 130 includes a total level display area A and an index display area B. In the case where the total level output from the determination processing part 112 is Level V, the output processing part 113 puts "V" in the total level display area A. The output processing part 113 also puts indices associated with the total level V in the total determination table 124 of FIG. 6 in the index display area B.

The output processing part 113 outputs the generated display screen 130 to the display part 13 (Step S13). This causes the display part 13 to display the display screen 130.

According to this embodiment, total binocular vision is evaluated from results of various tests and can be notified to the user. This allows the user to know the concrete level of his/her binocular vision and use the knowledge as reference in selecting digital contents or a product and in planning the length of viewing time.

Because the information presenting device 1 allows the user to know the level of his/her own binocular vision and three-dimensional intensity suitable for the user, creators of digital contents can produce digital contents high in three-dimensional intensity. Digital contents low in three-dimensional intensity have an advantage of being viewable by almost everyone, but also have a problem of not being satisfiable to people with great binocular vision. When users know the levels of their binocular vision and users with great binocular vision can select digital contents high in three-dimensional intensity, digital contents that satisfy many users can be produced. This is realized by producing, as a plurality of products, different versions of the same contents which differ from one another in three-dimensional intensity and writing the three-dimensional intensity on the package of each product on the part of digital contents creators.

While obtained test results are temporarily stored in the memory 902 in this embodiment, test results, obtained total score and total level, and the like may be stored in the storage part 12 in association with the name or ID of the user. When a user inputs an input instruction via the input part 14 in this case, the information management part 111 obtains the name or ID of the user via the input part 14, and can obtain test results, a total score, a total level, or the like that is associated with the user's name or ID.

Second Embodiment

A second embodiment of the present invention is a mode in which a product that matches a user's binocular vision is displayed on a display screen. An information presenting device 2 according to the second embodiment is described below. Components of the information presenting device 2 that are the same as those of the information presenting device 1 of the first embodiment are denoted by the same symbols, and descriptions thereof are omitted. The information presenting device 2 has the same hardware configuration as that of the information presenting device 1, and a description thereof is omitted.

Figure 11:
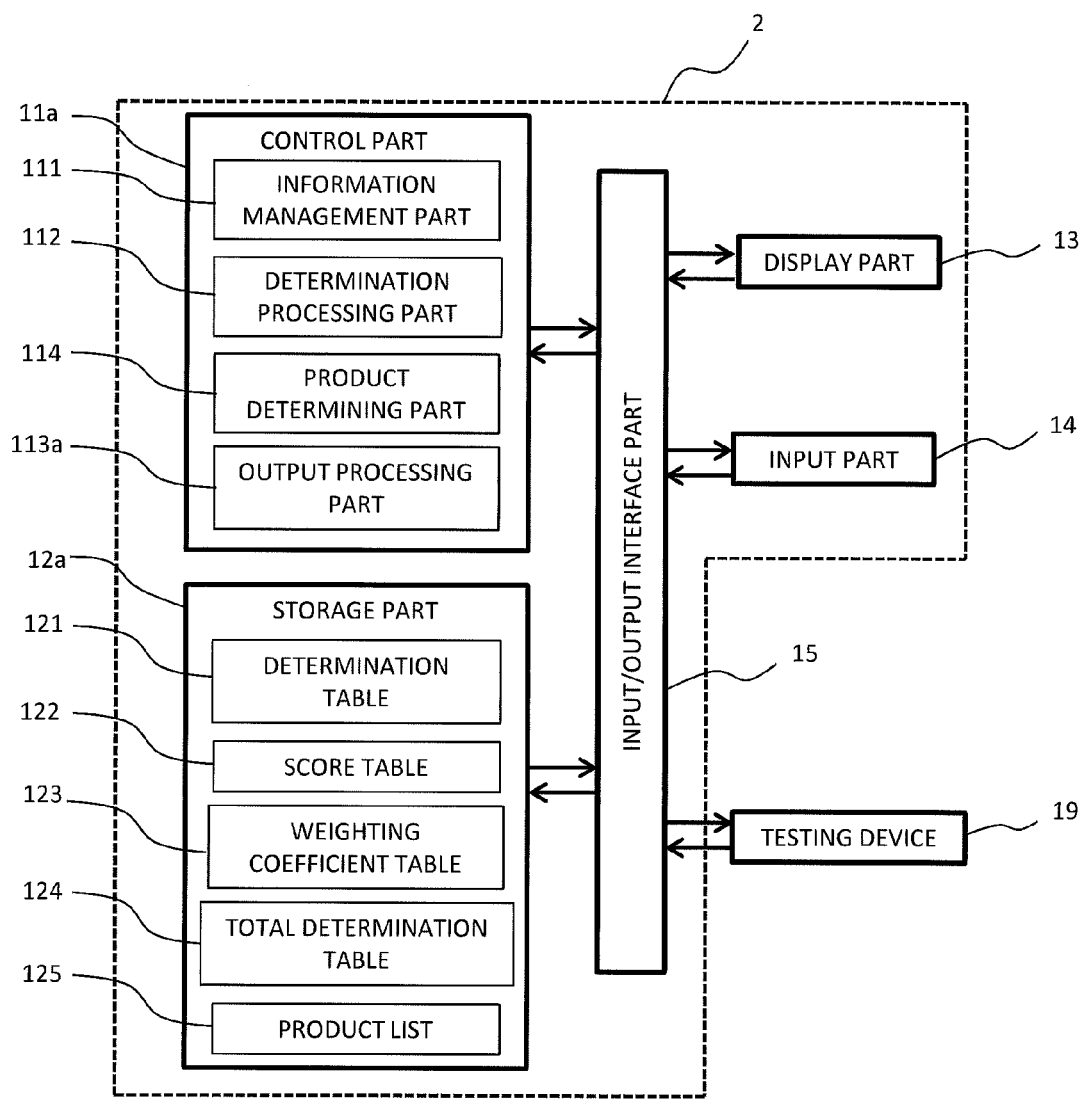
FIG. 11 is a schematic configuration diagram illustrating the configuration of an information presenting device 2 according to a second embodiment of the present invention.

FIG. 11 is a schematic configuration diagram illustrating the configuration of the information presenting device 2. The information presenting device 2 is a terminal set up at a storefront, in a workplace, or the like, or a portable terminal carried by a sales clerk or others, and includes a control part 11a, a storage part 12a, the display part 13, the input part 14, and the input/output interface part (hereinafter referred to as I/F part) 15. The information presenting device 2 is connected to one or more testing devices 19 directly or via a network (not shown). Not all components of the information presenting device 2 need to be in one place. For instance, the display part 13 and the input part 14 may be set up at a storefront to be connected by a wired or wireless network to the rest of the components which are set up at the back of the store or in an office.

The control part 11*a* includes the information management part 111 for handling overall information management, a determination processing part 112 for executing a determination program to determine stereoscopic vision from test results, a product determining part 114 for determining which product is to be suggested based on the result of the determination, and an output processing part 113*a* for outputting a result to the display part 13.

The product determining part 114 determines which product is to be suggested to the user based on the result of the determination made by the determination processing part 112. Details of the processing of the product determining part 114 are described later.

The output processing part 113*a* generates an output screen in which a product determined by the product determining part 114 is written, and outputs the generated screen to the display part 13. Details of the processing of the output processing part 113*a* are described later.

The storage part 12*a* stores in advance the determination table 121, which serves as a reference for evaluating a basic level in each test item, the score table 122 and the weighting coefficient table 123, which are used for converting the basic level in each test item into a score point, the total determination table 124, which is used for determining the total stereoscopic vision level from a score point, and a product list 125, which is used in determining a product.

FIG. 12 is a schematic explanatory diagram of the product list 125. The product list 125 includes a product name storing area 1251 for storing the name of each product, a total level storing area 1252 for storing a total level associated with the product, a product type storing area 1253 for storing the type of the product, and a product guide information storing area 1254 for storing information for introducing the product. Pieces of information in the respective storing areas of the product list 125 are associated with one another. Specifically, the name of a product, a total level, the type of the product, and information for introducing the product are stored in association with one another. Information stored in the product list 125 is not limited thereto, and the price of the product, information about the maker, and the like may further be stored. While "DVD" and "camera" are written as product types in FIG. 12, these are merely an example and "TV", "VTR", "DVD player", and the like are also included as product types.

Figure 13:
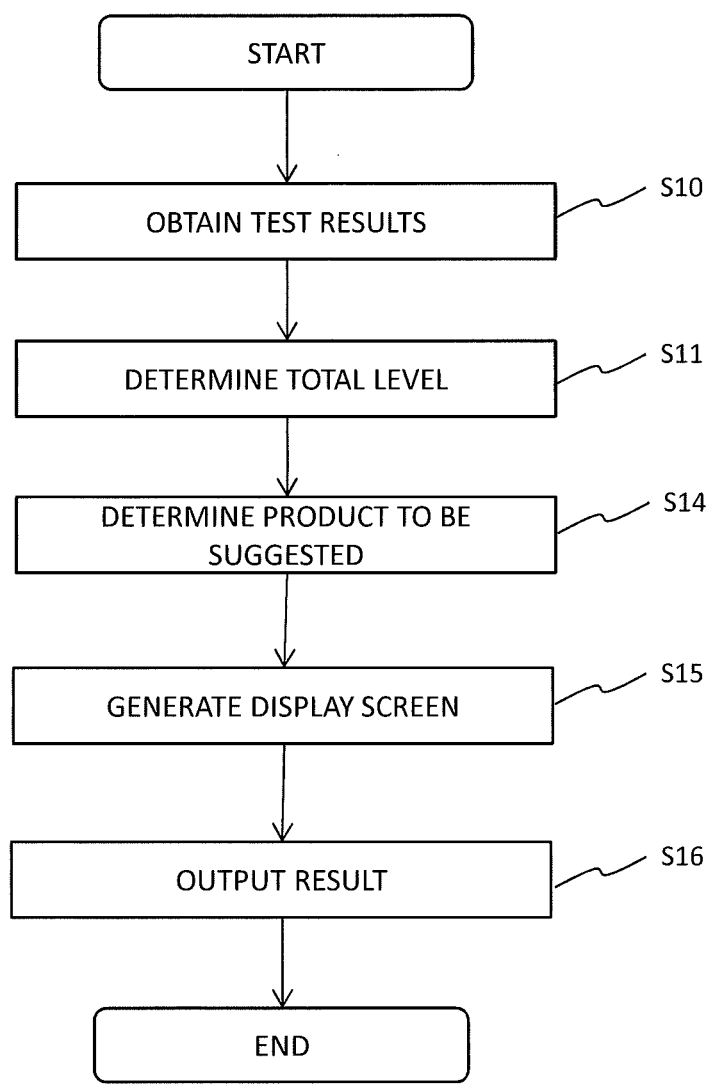

The operation of the thus configured information presenting device 2 is described with reference to a flow chart of FIG. 13. FIG. 13 is a flowchart illustrating the flow of processing that is executed by the information presenting device 2 according to this embodiment.

First, when an input instruction is input by a user via the input part 14, the information management part 111 outputs a test request to the testing device 19, and the determination processing part 112 obtains test results (see FIG. 2) output from the testing device 19 (Step S10).

The determination processing part 112 temporarily stores the obtained test results in the memory 902, and determines the total level based on the test results and on information stored in the storage part 12*a* (Step S11). The determination processing part 112 outputs the obtained total level to the product determining part 114.

The product determining part 114 obtains the total level output from the determination processing part 112, and determines a product to be suggested based on the obtained total level (Step S114). Specifically, the product determining part 114 obtains the product list 125 from the storage part 12 and determines, as a product to be suggested, each product that is associated with the obtained total level. The product determining part 114 also obtains the "product name", "product type", and "information for introducing the product" of the product from the product list 125. The product determining part 114 outputs the information related to the product to be suggested ("product name", "product type", and "information for introducing the product") to the output processing part 113*a*.

Figure 14:
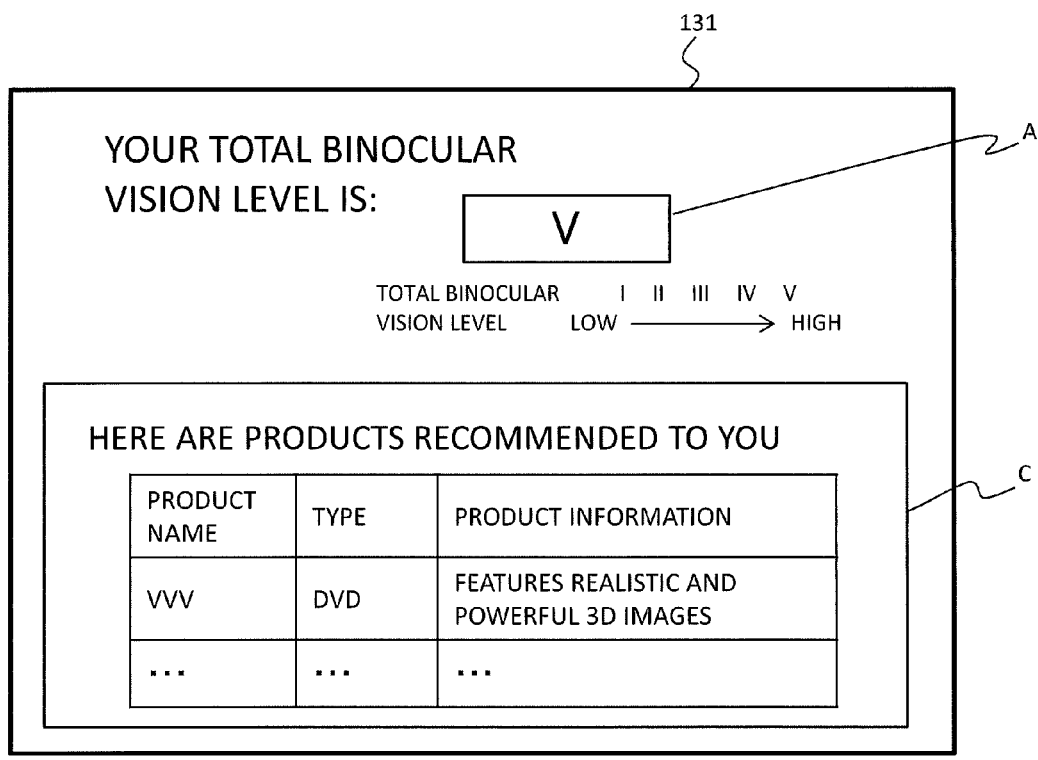
FIG. 14 is a schematic view of a display screen 131.

The output processing part 113*a* generates, based on the result output from the product determining part 114, a screen in which the obtained total level and a product associated with the total level are written (a display screen 131) (Step S15). FIG. 14 is an example of the display screen 131. The display screen 131 includes the total level display area A and a product display area C. In the case where the total level output from the determination processing part 112 is Level V, the output processing part 113*a* puts "V" in the total level display area A. The output processing part 113*a* also puts product-related information of the product determined in Step S14 in the product display area C. A product having a product name "VVV" is associated with Total Level V in the product list 125 of FIG. 12. The output processing part 113*a* therefore puts the product name "VVV" and a product type and product information that are associated with the product name "VVV" (here, a product type "DVD" and product information "features realistic and powerful 3D images") in the product display area C.

While all pieces of product-related information are put in the product display area C in FIG. 14, it is sufficient if minimum information necessary for users to recognize a product is put in the product display area C, and only some of product-related information may be put in the product display area C.

The output processing part 113*a* outputs the generated display screen 113 to the display part 13 (Step S16). This causes the display part 13 to display the display screen 131. The specifics of Step S16 are the same as those of Step S13.

According to this embodiment, a product suitable for a user's binocular vision and information related to the product can be presented to the user. This allows the user to select products and digital contents suitable for the user without needing to know the level of his/her binocular vision.

While the description of this embodiment takes a single device set up in a store or the like as an example, the display part 13 and the input part 14 may be provided in a user's terminal, with the control part 11*a*, the storage part 12*b*, and the I/F part 15 provided in a terminal in the store of a net shop to be connected via a network (not shown) to the user's terminal.

The display part 13 may display a Web page that contains a description on a product. A Web server (not shown) is connected to the information presenting device 2 via a network 17, and the control part 11*a* obtains from the Web server a Web page that contains a description on a product to be suggested based on product-related information, and outputs the Web page to the display part 13. The user can view a Web page on which a product suitable for the user is written in this manner.

Third Embodiment

A third embodiment of the present invention is a mode in which a three-dimensional image that matches a user's binocular vision is displayed on a display screen. An information presenting device 3 according to the third embodiment is described below. Components of the information presenting device 3 that are the same as those of the information presenting device 1 of the first embodiment are denoted by the same symbols, and descriptions thereof are omitted. The information presenting device 3 has the same hardware configuration as that of the information presenting device 1, and a description thereof is omitted.

Figure 15:
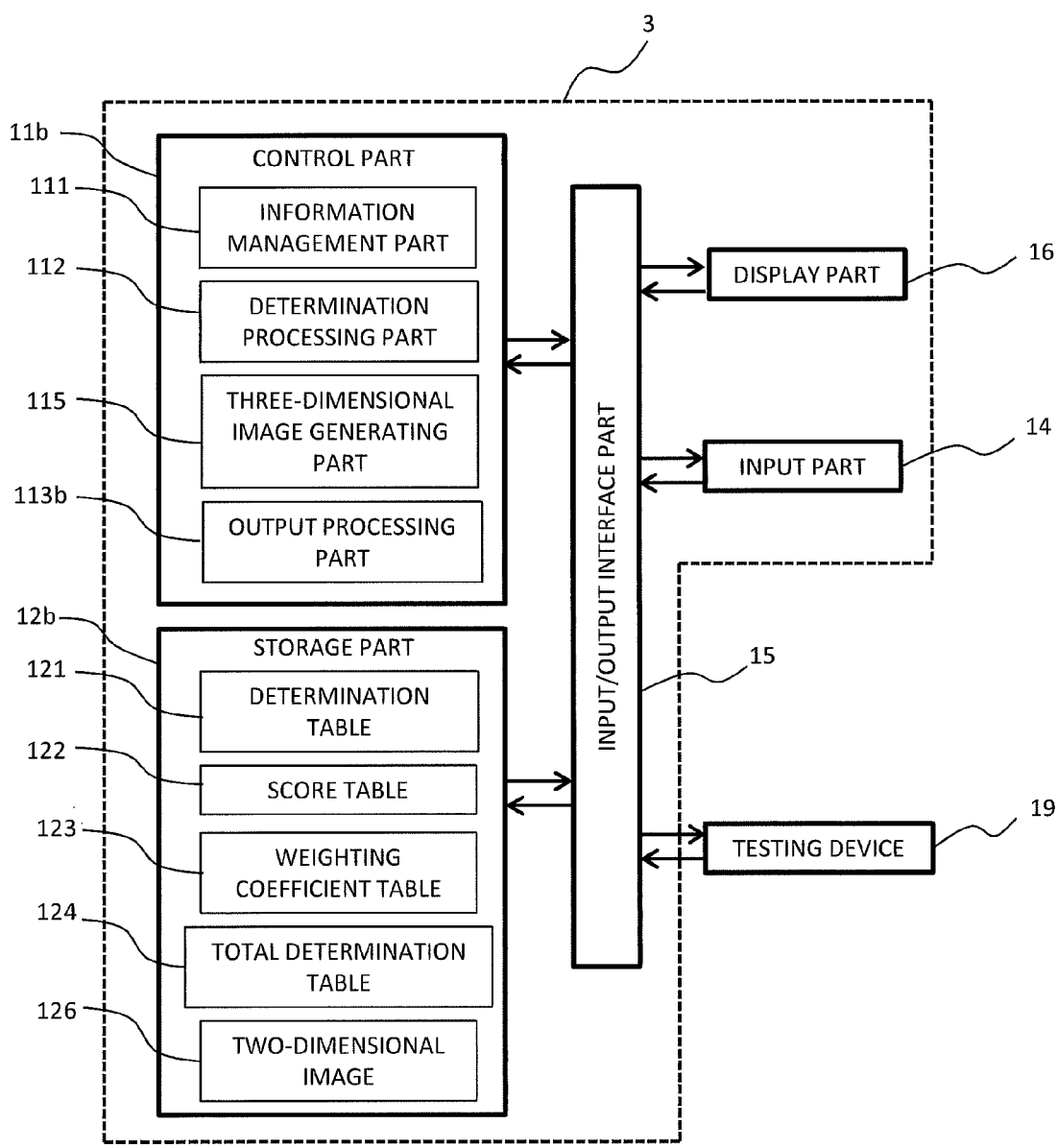
FIG. 15 is a schematic configuration diagram illustrating the configuration of an information presenting device 3 according to a third embodiment of the present invention.

FIG. 15 is a schematic configuration diagram illustrating the configuration of the information presenting device 3. The information presenting device 3 is a terminal set up in a home or a portable terminal, and includes a control part 11b, a storage part 12b, a display part 16, an input part 14, and an input/output interface part (hereinafter referred to as I/F part) 15. The information presenting device 3 is connected to one or more testing devices 19 directly or via a network (not shown). Not all components of the information presenting device 3 need to be in one place. For instance, the display part 16 and the input part 14 may be set up in a portable terminal to be connected by a wired or wireless network to the rest of the components which are set up in a stationary terminal.

The display part 16 is a parallax barrier monitor which is capable of switching between a mode for displaying three-dimensional images (3D mode) and a mode for displaying two-dimensional images (2D mode). A three-dimensional image is an image constructed from an image for the right eye and an image for the left eye. In the 3D mode, a parallax barrier having a pattern in which light transmitting portions and light blocking portions are alternated at given pitches is generated in a parallax barrier display layer of the display part 16, and strip-shaped fragments of a left image and a right image are arranged in an alternating manner to be displayed on an image display plane, which is placed under the parallax barrier display layer. An image for the right eye and an image for the left eye are thus displayed in a manner that makes the images recognizable as a three-dimensional image. In the 2D mode, or in the case where the monitor is used as a user interface display panel, nothing is displayed on the parallax barrier display layer and one whole image is directly displayed on the underlying image display plane.

The display part 16 is not limited to the parallax barrier type, and monitors of other types may be employed such as a lenticular type, an integral photography type which uses a micro-lens array sheet, a holography type which uses the interference phenomenon, and a polarized display type in which an image for the left eye and an image for the right eye are overlaid on top of each other on the same plane by polarization display and are separated from each other by polarization filter eyeglasses. In the case of the polarized display type, a normal monitor for displaying two-dimensional images may be used as the display part 16. The display part 16 is not limited to liquid crystal monitors, and an organic EL monitor or the like may be employed.

The control part 11b includes an information management part 111 for handling overall information management, a determination processing part 112 for executing a determination program to determine stereoscopic vision from test results, a three-dimensional image generating part 115 for generating a three-dimensional image based on the result of the determination on, and an output processing part 113b for outputting a result to the display part 13.

The three-dimensional image generating part 115 obtains a two-dimensional image and generates, from the two-dimensional image, a three-dimensional image based on the result of the determination made by the determination processing part 112. Details of the processing of the three-dimensional image generating part 115 are described later.

The output processing part 113b causes a parallax barrier in the display part 16, and concurrently generates display-use image data and outputs the generated data to the display part 16. The display-use image data is generated by dividing the three-dimensional image that the three-dimensional image generating part 115 has generated, namely, an image for the right eye and an image for the left eye which are used in replay, into strips and arranging the strips of the image for the right eye and the strips of the image for the left eye in an alternating manner.

The storage part 12b stores in advance the determination table 121, which serves as a reference for evaluating a basic level in each test item, the score table 122 and the weighting coefficient table 123, which are used for converting the basic level in each test item into a score point, the total determination table 124, which is used for determining the total stereoscopic vision level from a score point, and a two-dimensional image 126.

The two-dimensional image 126 is made up of a plurality of two-dimensional images photographed from a plurality of view points (hereinafter referred to as parallax images). A plurality of two-dimensional images 126 may be stored in the storage part 12b.

The location where two-dimensional images are stored does not need to be the storage part 12b. For instance, a two-dimensional image database storing two-dimensional images may be connected to the information presenting device 3 via the I/F part 15 and a network (not shown) so that the three-dimensional image generating part 115 obtains a two-dimensional image from the two-dimensional image database. Alternatively, a camera or a memory card in which two-dimensional images are stored may be connected to the information presenting device 3 via the I/F part 15 so that the three-dimensional image generating part 115 obtains a two-dimensional image from the camera or the memory card.

Figure 16:
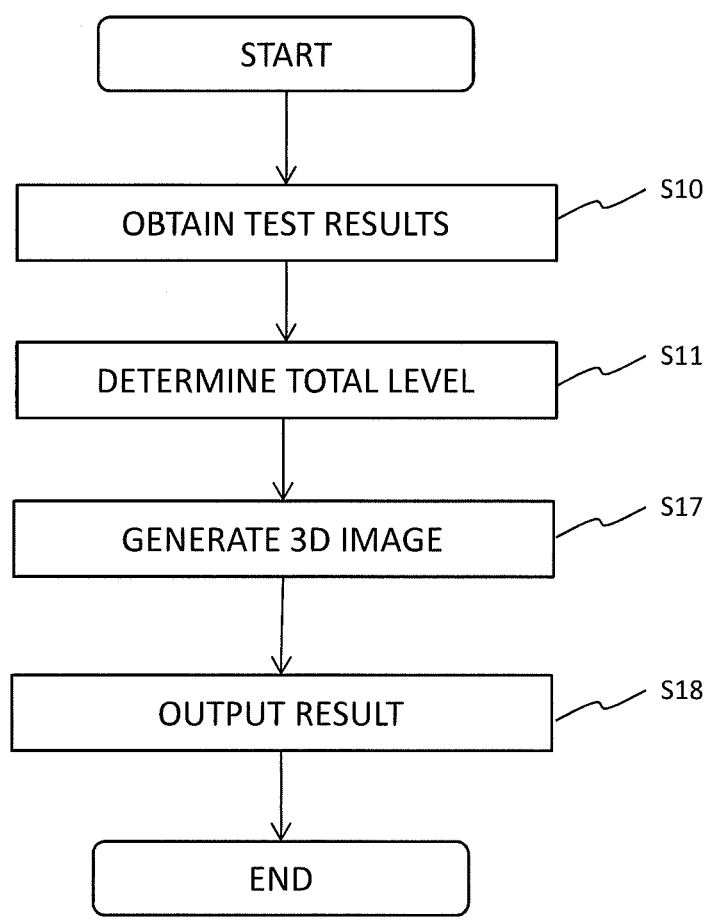
FIG. 16 is a flow chart illustrating processing that is executed by a control part 11b.

The operation of the thus configured information presenting device 3 is described with reference to a flow chart of FIG. 16. FIG. 16 is a flow chart illustrating the flow of processing that is executed by the information presenting device 3 according to this embodiment.

First, when an input instruction is input by a user via the input part 14, the information management part 111 outputs a test request to the testing device 19, and the determination processing part 112 obtains test results (see FIG. 2) output from the testing device 19 (Step S10).

The determination processing part 112 temporarily stores the obtained test results in the memory 902, and determines the total level based on the test results and on information stored in the storage part 12b (Step S11). The determination processing part 112 outputs the obtained total level to the three-dimensional image generating part 115.

The three-dimensional image generating part 115 obtains the total level output from the determination processing part 112 and the two-dimensional image 126, and generates from the two-dimensional image 126 a three-dimensional image suited to the obtained total level (Step S17). Step S17 is described below.

The three-dimensional image generating part 115 first obtains, from the plurality of parallax images, the coordinate values of a plurality of sets of feature points at which features match on the plurality of parallax images, and a parallax amount which is a differential between the coordinate values of the plurality of sets of feature points. Various methods of feature point detection have hitherto been proposed and block matching, for example, can be used.

The three-dimensional image generating part 115 next determines the position of a virtual view point so that the parallax amount increases when the three-dimensional intensity is to be enhanced and decreases when the three-dimensional intensity is to be lowered, and deforms the plurality of parallax images to generate an image for the left eye and an image for the right eye. For the geometric deformation, projection transformation which uses a projection transformation parameter, affine transformation which uses an affine transformation parameter, Helmert transformation which uses a Helmert transformation parameter, and the like can be used.

For example, the virtual view point is determined so that the parallactic angle is large (e.g., 2 degrees) in the case of Total Level I of FIG. 6. In the case of Total Level II and Total Level III, the virtual viewpoint is determined so that the parallactic angle is intermediate (e.g., 1 degree (1 degree equals 60 arcminutes)). In the case of Total Level IV, the virtual view point is determined so that the parallactic angle is small (e.g., 40 arcminutes). The parallactic angle is obtained by $\alpha$-$\beta$, which is a difference between an angle $\alpha$ and an angle $\beta$. The angle $\alpha$ is formed by a line that connects the position of the virtual view point of the right eye and a desired point (e.g., the center point) in the image for the right eye on the display, and a line that connects the position of the virtual view point of the left eye and the desired point (e.g., the center point) in the image for the right eye on the display. The angle $\beta$ is formed by a line that connects one point (point A) on the display and the position of the virtual view point of the right eye, and a line that connects the point A and the position of the virtual view point of the left eye.

The three-dimensional image generating part 115 may change the parallactic angle based on the total score, instead of on the total level. For example, the parallactic angle when the total score is 100 points is set as 2 degrees, the parallactic angle when the total score is 20 points is set as 0 degrees, and the parallactic angle is calculated as an angle that increases by 1.5 arcminutes for each increment of 1 point in total score from 20 points. The virtual view point is determined so that the calculated parallactic angle is reached. The three-dimensional image generating part 115 in this case obtains the total score calculated in Step S11.

The three-dimensional image generating part 115 may also generate a depth map from the plurality of two-dimensional images (or one of the plurality of two-dimensional images) to generate a three-dimensional image based on the depth map. A depth map indicates depth information and is drawn as an 8-bit grayscale image, for example. A depth map expresses the distance in an original image by drawing a portion on the near side in white and drawing a portion at the back in black. One of the plurality of two-dimensional images (for example, an image for the right eye) is chosen as the main image, a width by which an image is to be shifted from the main image (hereinafter referred to as shift amount) is determined based on distance information, which is obtained from the depth map, and another image (for example, an image for the left eye) is generated, to thereby generate a three-dimensional image.

In this case, the relation between a distance indicated by the depth map and a shift amount is stored in the storage part 12*b*. Based on the stored relation, the three-dimensional image generating part 115 calculates for each pixel an amount by which the pixel is to be shifted (hereinafter referred to as temporary shift amount). The three-dimensional image generating part 115 corrects the temporary shift amount based on the total level or the total score, and determines the shift amount used to generate a three-dimensional image. The temporary shift amount is corrected by, for example, multiplying the temporary shift amount by 1 when the total score is 100 points and multiplying the temporary shift amount by 0.2 when the total score is 20 points.

The processing described here in which the three-dimensional image generating part 115 generates a three-dimensional image is merely an example. The three-dimensional image generating part 115 can use one selected from a plurality of known methods of generating a three-dimensional image.

Figure 17:
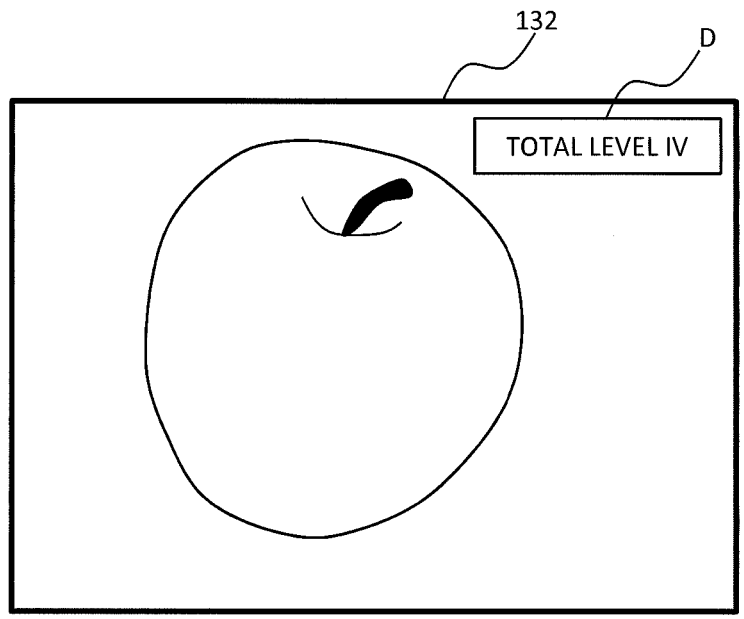
FIG. 17 is a schematic view of a display screen 132.

The output processing part 113*b* outputs the generated image for the left eye and the generated image for the right eye to the display part 16, and concurrently causes a parallax barrier (Step S18). The display part 16 thus displays the three-dimensional image. As illustrated in FIG. 17, a displayed image 132 of the display part 16 may include total level display D. The total level display D can be two-dimensional or three-dimensional.

According to this embodiment, a three-dimensional image suitable for a user's binocular vision can be generated and displayed. This allows the user to view a three-dimensional image that has a stereoscopic effect suitable for the user without needing to know the level of his/her binocular vision.

This embodiment is also applicable to cameras (not limited to cameras that are capable of photographing a three-dimensional image). The configuration of the information presenting device 3 may be added to a camera so that the three-dimensional image generating part 115 obtains two-dimensional images photographed by the camera, and generates a three-dimensional image to be displayed on a monitor that is provided on the back of the camera, or an external monitor connected to the camera.

In the case where the configuration of the information presenting device 3 is added to a camera, the processing of obtaining the photographer's binocular vision (Step S10) and the processing of determining the total level (Step S12) may be executed prior to photographing, and a three-dimensional image suitable for the photographer's binocular vision may be photographed instead of executing Step S17 and output (Step S18).

A three-dimensional camera that is capable of photographing a plurality of images having a parallax in one shot can be used to photograph a three-dimensional image. Known three-dimensional cameras include monocular three-dimensional cameras, which are capable of varying stereoscopic effect by changing the aperture opening size. In monocular three-dimensional cameras having such properties, the parallax of a subject in focus is 0, and the parallax increases as deviation from the in-focus point grows. The control part 11*b* in this case calculates an aperture opening amount that provides a stereoscopic effect suitable for the photographer's binocular vision, and outputs the calculated aperture opening amount to a control part of the camera. The control part of the camera controls the aperture opening amount and then photographs a three-dimensional image. The control part 11*b* only needs to obtain the photographed image.

Other known three-dimensional cameras than monocular three-dimensional cameras, which have a single taking lens, include multi-lens three-dimensional cameras which have a plurality of taking lenses and imaging elements. A camera of this type can vary the parallax of a three-dimensional image by, for example, having a configuration in which folded optics is used and the convergence angle is changed by turning of the folded optics inside the camera, or the base length is changed through the parallel displacement of the folded optics. The control part 11b in this case calculates a convergence angle/base length that provides a stereoscopic effect suitable for the photographer's binocular vision, and outputs the calculated convergence angle/base length to a control part of the camera. The control part of the camera moves/turns the imaging part so that the convergence angle or the base length has the calculated value, and then photographs a three-dimensional image. The control part 11b only needs to obtain the photographed image.

A three-dimensional image can also be photographed with the use of a common camera, instead of a three-dimensional camera. For instance, two images having a parallax can be photographed by photographing the first image and then moving the camera in the left-right direction to photograph the second image. More than two images can be photographed by repeating this operation. In the description given here, the number of images photographed is two.

When a normal camera is used to photograph a three-dimensional image, a control part of the camera uses a sensor for measuring the amount of movement of the camera, such as a GPS or an acceleration sensor, to obtain the camera movement amount. The control part of the camera also controls the camera overall so that the second image is automatically photographed if the camera is moved by a given movement amount when the photographer carrying the camera moves after photographing the first image.

The parallax of the two images is changed by changing the amount by which the camera is moved in the left-right direction (hereinafter referred to as slide amount). Specifically, the two images have a small parallax when the slide amount is small and have a large parallax when the slide amount is large. The control part 11b sets the slide amount so that a stereoscopic effect suitable for the photographer's binocular vision is provided, and outputs the thus set slide amount to the control part of the camera.

In an alternative mode, the slide amount is displayed on a monitor of the camera or the like in order to assist the photographer in photographing. The control part of the camera in this case merely displays the slide amount on the monitor. The control part of the camera may instead display guidance for assisting the photographer in moving the camera by the set slide amount on the monitor, or output audio guidance.

Fourth Embodiment

The information presenting devices 1 to 3 take a mode in which the information presenting device is provided as a terminal set up at a storefront, in a workplace, a user's home, or the like, or as a portable terminal carried by a sales clerk, a user, or others. An information presenting device of the present invention may also be provided as a system that includes a server and a terminal. An information presenting system 4 according to a fourth embodiment of the present invention is described below. Components of the information presenting system 4 that are the same as those of the information presenting device 1 of the first embodiment are denoted by the same symbols, and descriptions thereof are omitted. The server and the terminal that construct the information presenting system 4 have the same hardware configuration as that of the information presenting device 1, and a description thereof is omitted.

Figure 18:
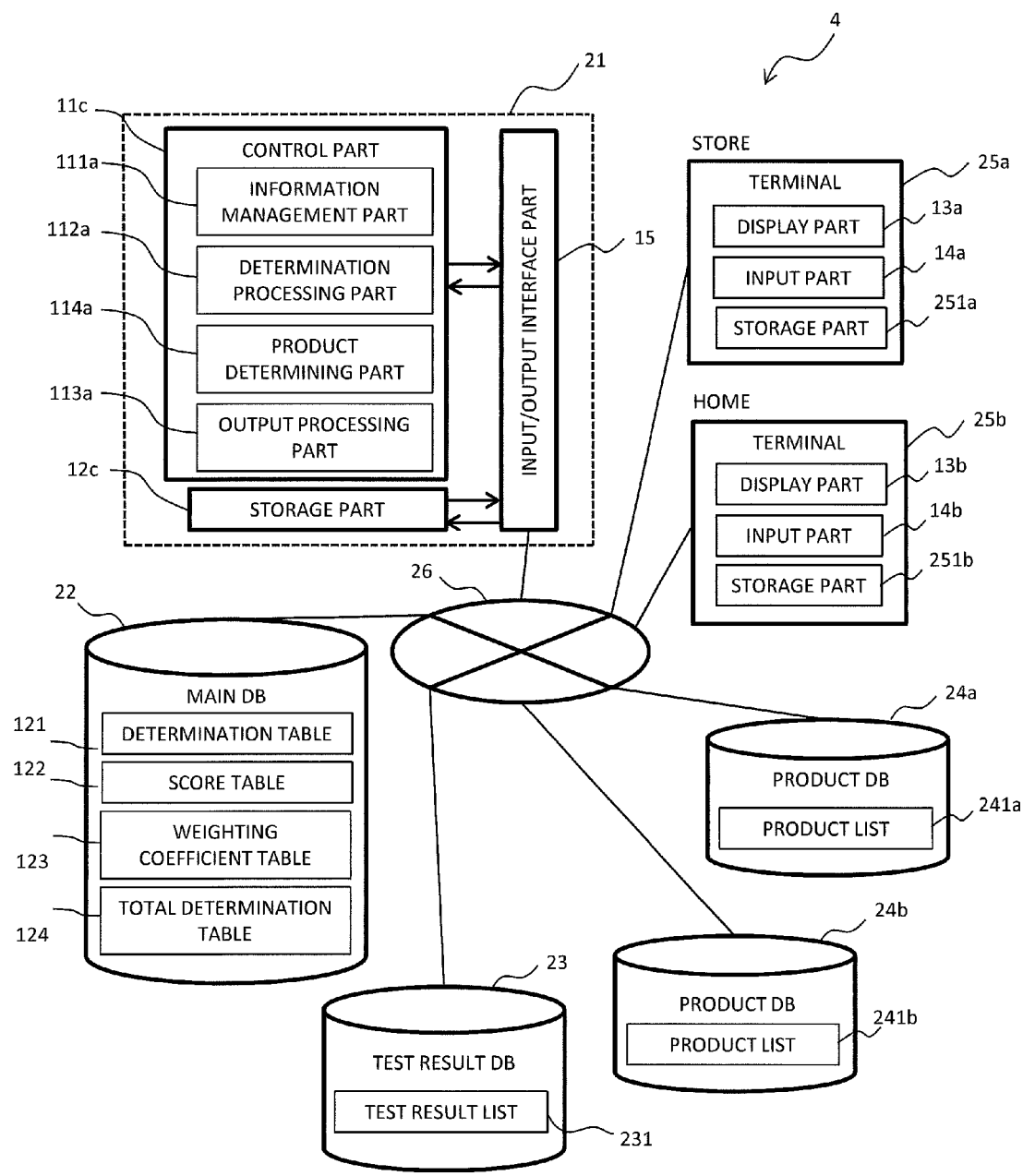
FIG. 18 is a schematic configuration diagram illustrating the configuration of an information presenting system 4 according to a fourth embodiment of the present invention.

FIG. 18 is a schematic diagram of the information presenting system 4 according to an embodiment of the present invention. The information presenting system 4 includes a server 21, a main database (hereinafter abbreviated as DB) 22, a test result DB 23, and product DBs 24a, 24b . . . (product DBs 24 in the following description when it is not particularly necessary to discriminate one product DB from another), and a plurality of terminals 25a, 25b . . . (terminals 25 in the following description when it is not particularly necessary to discriminate one terminal from another), which are capable of transmitting/receiving information to/from one another via a network 26. While FIG. 18 shows two product DBs 24 and two terminals 25, the number of the product DBs 24 and the number of the terminals 25 are not limited to two.

The terminals 25 are each a terminal set up in a store (for example, an appliance dealer's store, a store selling digital contents, or an eyewear store) or in a home, or a portable terminal, and includes the display part 13, the input part 14, and a storage part 251 for storing information unique to the terminal such as a terminal ID. The store is not limited to an actual store and can be an online store on the Internet.

The server 21 includes a control part 11c, a storage part 12c, and the I/F part 15. The control part 11c includes an information management part 111a for handling overall information management, a determination processing part 112a for executing a determination program to determine stereoscopic vision from test results, a product determining part 114a for determining which product is to be suggested based on the result of the determination, and the output processing part 113a for outputting a result to the display part 13.

The storage part 12c stores, in advance, information that associates the terminal 25 with one of the product DBs 24. For example, the terminal 25a is associated with the product DB 24a and the terminal 25b is associated with the product DB 24b.

The main DB 22 stores in advance the determination table 121, which serves as a reference for evaluating a basic level in each test item, the score table 122 and the weighting coefficient table 123, which are used for converting the basic level in each test item into a score point, the total determination table 124, which is used for determining the total stereoscopic vision level from a score point, and the product list 125, which is used in determining a product.

The test result DB 23 stores a test result list 231. FIG. 19 is a schematic explanatory diagram of the test result list 231. The test result list 231 includes a user information storing area 2311 for storing, for each user, information about the user, and a test result storing area 2312 for storing test results of the user. The user information storing area 2311 stores for each user the name of the user and a user ID. The test result storing area 2312 stores the same data as shown in FIG. 2, and a description thereof is therefore omitted. Pieces of information in the respective storing areas of the test result list 231 are associated with each other. Specifically, information about a user and test results of the user are stored in association with each other.

The product DBs 24 each store a product list 241 in advance. For example, the product DB 24a stores a product list 241a and the product DB 24b stores a product list 241b. The product list 241 for an appliance dealer, for example, stores pieces of hardware equipment such as TVs, DVD recorders, and cameras as products. The product list 241 for an eyewear store stores eyeglasses as products. The product list 241 for a store that sells or lends digital contents, or deals in other forms of digital contents business, stores DVDs and other types of software as products. The product list 241a, the product list 241b . . . store different data (different types of products). The configuration of the product lists 241 is the same as that of the product list 125, and a description thereof is omitted.

Figure 20:
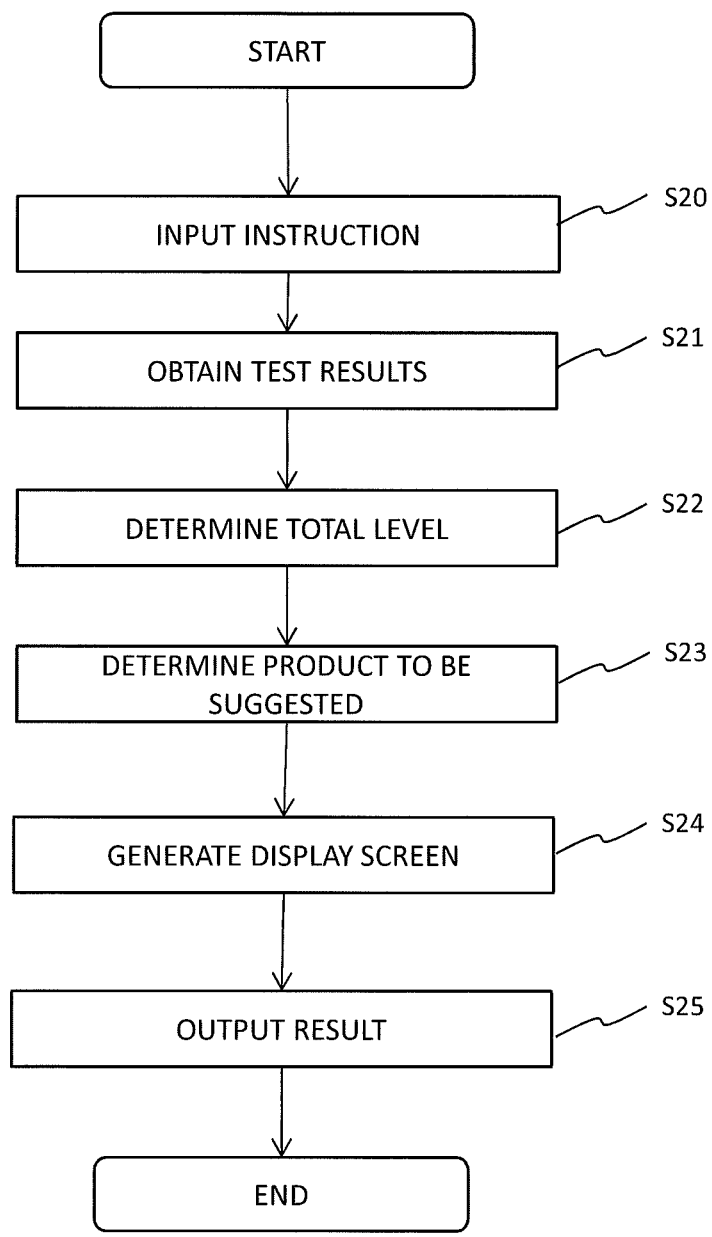
FIG. 20 is a flow chart illustrating processing that is executed by a control part 11c.

The operation of the thus configured information presenting system 4 is described with reference to a flow chart of FIG. 20. FIG. 20 is a flow chart illustrating the flow of processing that is executed by the information presenting system 4 according to this embodiment.

When a user of one of the terminals 25 inputs an input instruction via the input part 14 of the terminal 25, the information management part 111a determines from which terminal 25 the input has been made. The information management part 111a also outputs an instruction to the terminal 25 from which the input has been made in order to instruct the terminal 25 to input information about the user (Step S20). When information about the user is input via the input part 14, the information management part 111a outputs the information to the determination processing part 112a. The information management part 111a also outputs, to the product determining part 114a, information about the terminal 25 from which the input has been made (for example, information indicating that an input has been made from the terminal 25a).

The determination processing part 112a obtains the information about the user and obtains, from the test result DB 23, test results of the user whose information has been input (Step S21). Specifically, the determination processing part 112a refers to the test result list 231 to obtain test results that are associated with the obtained user name or user ID.

The determination processing part 112a temporarily stores the obtained test results in the memory 902, and determines the total level based on the test results and on information stored in the main DB 22 (Step S22). The determination processing part 112a outputs the obtained total level to the product determining part 114a. The processing of Step S22 is the same as that of Step S11 of the first embodiment.

The product determining part 114a obtains the total level output from the determination processing part 112a, and determines a product to be suggested based on the obtained total level (Step S23). Processing of Step S23 is described below.

The product determining part 114a obtains the information about the terminal 25 from which the input has been made, and determines, based on information stored in the storage part 12c, from which product DB 24 the product list 241 is to be obtained. For example, in the case where the terminal 25a is associated with the product DB 24a, the product list 241a of the product DB 24a is obtained when it is the terminal 25 that has made the input.

Based on the product list 241, the product determining part 114a determines a product that is associated with the total level obtained in Step S11 as a product to be suggested. The product determining part 114a also obtains the "product name", "product type", and "information for introducing the product" of this product from the product list 241. The product determining part 114a outputs the information related to the product to be suggested ("product name", "product type", and "information for introducing the product") to the output processing part 113a.

The output processing part 113a generates, based on the result output from the product determining part 114a, a screen in which the obtained total level and a product associated with the total level are written (Step S24). The output processing part 113a outputs the generated display screen to the display part 13 (Step S25). This causes the display part 13 to display the display screen. Step S24 is the same as Step S15 of the second embodiment, and Step S25 is the same as Step S13 of the first embodiment.

According to this embodiment, a product suitable for a user's binocular vision and information about the product can be presented to the user even when the distance between the server and a store is great or in the case of net shopping where the user shops on the Internet. This allows the user to select products and digital contents suitable for the user without needing to know the level of his/her binocular vision.

Figure 21:
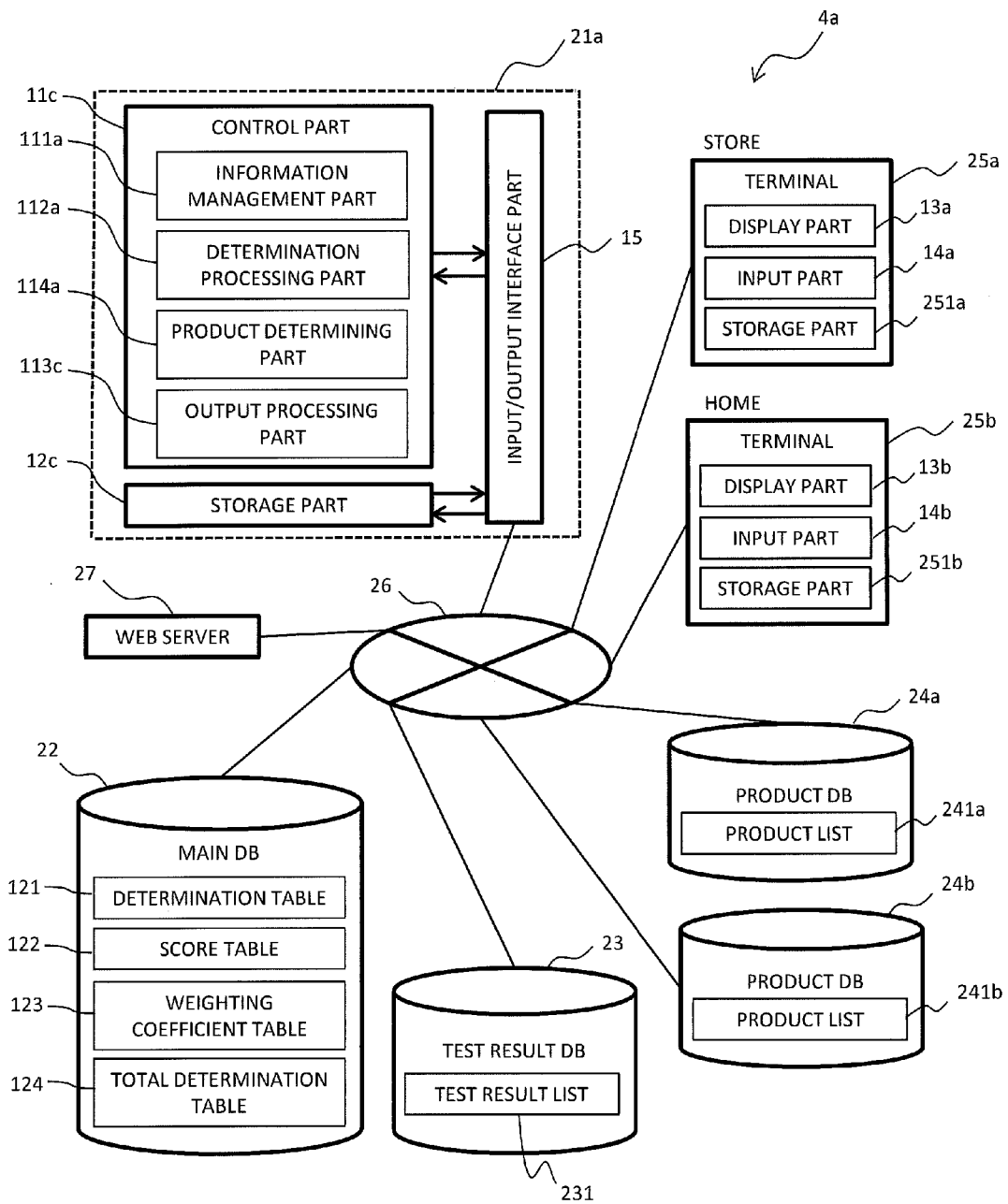
FIG. 21 is a schematic configuration diagram illustrating the configuration of an information presenting system 4a, which is a modification example of the information presenting system 4.

While a screen in which a product associated with a determined total level is written is output to the display part 13 in this embodiment, the display part 13 may display a Web page that contains a description on the product. FIG. 21 is a schematic configuration diagram of a information presenting system 4a according to a modification example of this embodiment. In the information presenting system 4a, a Web server 27 is connected to a server 21a via the network 17. Instead of executing Step S15, an output processing part 113c obtains from the Web server 27 a Web page that contains a description on a product to be suggested based on product-related information, and outputs the Web page to the display part 13. The user can view a Web page on which a product suitable for the user is written in this manner. Various known technologies can be used as a method of obtaining from the Web server 27 a Web page that contains a description on a product to be suggested based on product-related information.

The output processing part 113a may generate a display screen in which a product associated with the obtained total level is written to display the display screen on the display part 13 (Steps S15 and S13), and, when a Web page viewing request is input via the input part 14, may obtain from the Web server 27 a Web page that contains a description on a product to be suggested based on product-related information to output the Web page to the display part 13.

Embodiments of the present invention have been described in detail with reference to the drawings. However, the concrete configuration of the present invention is not limited to the embodiments, and includes design changes and the like that do not depart from the spirit of the present invention. The present invention is not limited to information presenting devices, and may be provided as a system that includes a plurality of devices, or may be provided as a program to be applied to various devices such as personal computers, TVs, cameras, and portable terminals.

REFERENCE SIGNS LIST 1, 2, 3: information presenting device, 4: information presenting system, 11a, 11b: control part, 12a, 12b: storage part, 13, 16: display part, 14: input part, 15: I/F part, 19: testing device, 21: server, 22: main DB, 23: test result DB, 24, 24a, 24b: product DB, 25, 25a, 25b: terminal, 26: network, 111, 111a: information management part, 112, 112a: determination processing part, 113, 113a: output processing part, 114, 114a: product determining part, 115: three-dimensional image generating part, 121: determination table, 122: score table, 123: weighting coefficient table, 124: total determination table, 125: product list, 126: two-dimensional image, 130, 131, 132: displayed image, 231: test result list, 241, 241a, 241b: product list, 902: memory, 903: external storage device, 904: display device, 905: input device, 906: communication device, 907: bus

The invention claimed is:

1. An information presenting device, comprising:
an obtaining part adapted to obtain results of tests related to a user's binocular vision;
a classifying part adapted to classify based on the obtained test results, the user's binocular vision into one of a plurality of classes; and
an output part adapted to output total level information suited to the user's binocular vision, based on the class into which the user's binocular vision is classified, to display part,
wherein:
(i) the test results obtained by the obtaining part comprise results of at least two test items selected from a stereo test, an accommodation time measuring test, a flicker test, a duration measuring test, a break strength measuring test, a left/right eye rotation angle measuring test, and a visual depth activity measuring test,
(ii) the classifying part calculates a temporary score point for each of the at least two test items, calculates a systematical score based on the calculated temporary score points, and classifies the user's binocular vision into one of the plurality of classes based on the calculated systematical score, and
(iii) the classifying part calculates the systematical score by multiplying the temporary score points by weighting coefficients that are associated with the test items, and adding up the weighted score points.

2. An information presenting device according to claim 1, wherein the output part outputs, as the information suited to the user's binocular vision, information that indicates the class into which the user's binocular vision is classified.

3. An information presenting device according to claim 1, further comprising:
a storage part adapted to store information related to a product in association with an appropriate one of the plurality of classes; and
a product determining part adapted to determine a product suitable for the user based on the class into which the user's binocular vision is classified and the information stored in the storage part,
wherein the output part outputs information related to the determined product as the information suited to the user's binocular vision.

4. An information presenting device according to claim 3, wherein the information related to a product comprises at least one of a product name, a product type, and information introducing the product.

5. An information presenting device according to claim 3, further comprising:
a Web server for providing a Web page;
an input part adapted to input a request to view detailed information of the determined product; and
a Web page obtaining part adapted to obtain when the viewing request is input by the input part, a Web page that contains a description about the determined product from the Web server,
wherein the output part outputs the obtained Web page to the display part.

6. An information presenting device according to claim 1, further comprising:
a two dimensional image obtaining part adapted to obtain two-dimensional images; and
a three-dimensional image generating part adapted to generate based on the class into which the user's binocular vision is classified, from the obtained two-dimensional images, a three-dimensional image suitable for the class of binocular vision into which the user's binocular vision is classified,
wherein the output part outputs the generated three-dimensional image as the information suited to the user's binocular vision.

7. An information presenting device according to claim 6, wherein the three-dimensional image generating part generates a three-dimensional image so that a parallactic angle associated with the class into which the user's binocular vision is classified by the classifying part is reached.

8. An information presenting system, comprising:
a terminal device; and
a server connected to the terminal device,
the server comprising:
an obtaining part adapted to obtain results of tests related to a user's binocular vision;
a classifying part adapted to classify, based on the obtained test results, the user's binocular vision into one of a plurality of classes; and
an output part adapted to output total level information suited to the user's binocular vision, based on the class into which the user's binocular vision is classified, to the terminal device,
wherein:
(i) the test results obtained by the obtaining part comprise results of at least two test items selected from a stereo test, an accommodation time measuring test, a flicker test, a duration measuring test, a break strength measuring test, a left/right eye rotation angle measuring test, and a visual depth activity measuring test,
(ii) the classifying part calculates a temporary score point for each of the at least two test items, calculates a systematical score based on the calculated temporary score points, and classifies the user's binocular vision into one of the plurality of classes based on the calculated systematical score, and
(iii) the classifying part calculates the systematical score by multiplying the temporary score points by weighting coefficients that are associated with the test items, and adding up the weighted score points.

9. An information presenting system according to claim 8, further comprising a Web server for providing a Web page,
wherein the server further comprises:
a storage part adapted to store information related to a product in association with an appropriate one of the plurality of classes;
a product determining part adapted to determine a product suitable for the user based on a class into which the user's binocular vision is classified and the information stored in the storage part; and
a Web page obtaining part adapted to obtain a Web page that contains a description about the determined product from the Web server,
wherein the output part outputs the obtained Web page to the terminal device total level information suited to the user's binocular vision,
wherein:
(i) the test results obtained by the obtaining part comprise results of at least two test items selected from a stereo test, an accommodation time measuring test, a flicker test, a duration measuring test, a break strength measuring test, a left/right eye rotation angle measuring test, and a visual depth activity measuring test,
(ii) the classifying part calculates a temporary score point for each of the at least two test items, calculates a systematical score based on the calculated temporary score points, and classifies the user's binocular vision into one of the plurality of classes based on the calculated systematical score, and
(iii) the classifying part calculates the systematical score by multiplying the temporary score points by weighting coefficients that are associated with the test items, and adding up the weighted score points.

10. A server, which is a constituent of the information presenting system according to claim 8.

11. An information presenting method, comprising the steps of:
obtaining results of tests related to a user's binocular vision;
a classifying, based on the obtained test results, the user's binocular vision into one of a plurality of classes; and
outputting total level information suited to the user's binocular vision, based on the class into which the user's binocular vision is classified,
wherein:
(i) the obtained test results comprise results of at least two test item selected from a stereo test, an accommodation time measuring test, a flicker test, a duration measuring test, a break strength measuring test, a left/right eye rotation angle measuring test, and a visual depth acuity measuring test,
(ii) a temporary score point is calculated for each of the at least two test items, a systematical score is calculated based on the calculated temporary score points, and classifies the user's binocular vision into one of the plurality of classes based on the calculated systematical score, and
(iii) the classifying part calculates the systematical score by multiplying the temporary score points by weighting coefficients that are associated with the test items, and adding up the weighted score points.

12. A computer program product comprising a non-transitorily computer-readable medium having executable programming insturctions stored thereon that, when executed, causes a computer to function as an information presenting device, the computer program product causing the computer to execute the steps of:
obtaining results of tests related to a user's binocular vision;
classifying, based on the obtained test results, the user's binocular vision into one of a plurality of classes; and
outputting total level information suited to the user's binocular vision, based on the class into which the user's binocular vision is classified,
wherein:
(i) the obtained test results comprise results of at least two test item selected from a stereo test, an accommodation time measuring test, a flicker test, a duration measuring test, a break strength measuring test, a left/right eye rotation angle measuring test, and a visual depth acuity measuring test,
(ii) a temporary score point is calculated for each of the at least two test items, a systematical score is calculated based on the calculated temporary score points, and classifies the user's binocular vision into one of the plurality of classes based on the calculated systematical score, and
(iii) the classifying part calculates the systematical score by multiplying the temporary score points by weighting coefficients that are associated with the test items, and adding up the weighted score points.

* * * * *